(12) United States Patent
Fornwalt et al.

(10) Patent No.: US 12,176,111 B2
(45) Date of Patent: *Dec. 24, 2024

(54) SYSTEMS AND METHODS FOR MACHINE LEARNING APPROACHES TO MANAGEMENT OF HEALTHCARE POPULATIONS

(71) Applicant: Geisinger Clinic, Danville, PA (US)

(72) Inventors: Brandon K. Fornwalt, Lewisburg, PA (US); Christopher Haggerty, Lewisburg, PA (US); Linyuan Jing, Danville, PA (US)

(73) Assignee: Geisinger Clinic, Danville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/071,592

(22) Filed: Nov. 29, 2022

(65) Prior Publication Data

US 2023/0087969 A1    Mar. 23, 2023

Related U.S. Application Data

(63) Continuation of application No. 17/098,552, filed on Nov. 16, 2020, now Pat. No. 11,515,040.

(Continued)

(51) Int. Cl.
*G16H 50/20* (2018.01)
*A61B 5/00* (2006.01)
(Continued)

(52) U.S. Cl.
CPC ............ *G16H 50/20* (2018.01); *A61B 5/486* (2013.01); *A61B 5/7267* (2013.01);
(Continued)

(58) Field of Classification Search
CPC ........ G16H 50/20; G16H 40/20; G16H 50/50; G16H 10/60; G16H 15/00; G16H 50/30;
(Continued)

(56) References Cited

U.S. PATENT DOCUMENTS 10,485,489 B1 * 11/2019 Belle ...................... A61B 5/339
11,515,040 B2 * 11/2022 Fornwalt .............. A61B 8/0883
(Continued)

FOREIGN PATENT DOCUMENTS

WO    2004015608 A2    2/2014
WO    WO-2015157577 A2 * 10/2015 ............. G06Q 10/06

OTHER PUBLICATIONS

Azur, M. et al., Multiple Imputation by Chained Equations: What Is It and How Does It Work?, International Journal of Methods in Psychiatric Research, 2011, 20(1):40-49.

(Continued)

*Primary Examiner* — Michael Tomaszewski
(74) *Attorney, Agent, or Firm* — Quarles & Brady LLP

(57) ABSTRACT

A method for providing treatment recommendations for a patient to a physician is disclosed. The method includes receiving health information associated with the patient, determining a first risk score for the patient based on the health information using a trained predictor model, determining a second risk score for the patient based on the health information and at least one artificially closed care gap included in the health information using the predictor model, determining a predicted risk reduction score based on the first risk score and the second risk score, determining a patient classification based on the predicted risk reduction score, and outputting a report based on at least one of the first risk score, the second risk score, or the predicted risk reduction score.

28 Claims, 9 Drawing Sheets

Related U.S. Application Data

(60) Provisional application No. 62/936,374, filed on Nov. 15, 2019.

(51) Int. Cl.
| | | |
|---|---|---|
| *A61B 8/08* | (2006.01) | |
| *G06N 20/00* | (2019.01) | |
| *G16H 10/20* | (2018.01) | |
| *G16H 10/60* | (2018.01) | |
| *G16H 15/00* | (2018.01) | |
| *G16H 40/20* | (2018.01) | |
| *G16H 50/30* | (2018.01) | |
| *G16H 50/50* | (2018.01) | |
| *G16H 50/70* | (2018.01) | |
| *A61B 5/33* | (2021.01) | |

(52) U.S. Cl.
CPC .......... *A61B 5/7275* (2013.01); *A61B 8/0883* (2013.01); *G06N 20/00* (2019.01); *G16H 10/20* (2018.01); *G16H 10/60* (2018.01); *G16H 15/00* (2018.01); *G16H 40/20* (2018.01); *G16H 50/30* (2018.01); *G16H 50/50* (2018.01); *G16H 50/70* (2018.01); *A61B 5/33* (2021.01)

(58) Field of Classification Search
CPC ........ G16H 50/70; G16H 10/20; G06N 20/00; A61B 5/486; A61B 5/7267; A61B 5/7275; A61B 8/0883
USPC .......................................................... 705/2–3
See application file for complete search history.

(56) References Cited

U.S. PATENT DOCUMENTS

| | | | |
|---|---|---|---|
| 11,972,869 B2 | 4/2024 | Wagner et al. | |
| 2002/0123906 A1* | 9/2002 | Goetzke | G16H 50/20 705/2 |
| 2007/0214013 A1 | 9/2007 | Silverman | |
| 2011/0105852 A1* | 5/2011 | Morris | G06Q 10/10 600/300 |
| 2011/0295621 A1* | 12/2011 | Farooq | G16H 50/20 705/3 |
| 2015/0106123 A1* | 4/2015 | Amarasingham | G06Q 50/01 705/3 |
| 2015/0213202 A1* | 7/2015 | Amarasingham | G16Z 99/00 705/2 |
| 2015/0213206 A1* | 7/2015 | Amarasingham | G16H 50/30 705/2 |
| 2015/0213207 A1* | 7/2015 | Amarasingham | G16H 50/50 705/2 |
| 2015/0213217 A1* | 7/2015 | Amarasingham | G16H 50/30 705/2 |
| 2015/0213222 A1* | 7/2015 | Amarasingham | G16H 50/30 705/2 |
| 2015/0213223 A1* | 7/2015 | Amarasingham | G16H 50/30 705/2 |
| 2015/0213224 A1* | 7/2015 | Amarasingham | G16H 50/30 705/2 |
| 2015/0213225 A1* | 7/2015 | Amarasingham | G16H 50/30 705/2 |
| 2015/0363568 A1* | 12/2015 | Milo | G16H 50/30 705/2 |
| 2016/0378943 A1* | 12/2016 | Vallée | G16H 40/63 705/2 |
| 2018/0173854 A1* | 6/2018 | Kailasam | G16H 50/20 |
| 2018/0308584 A1* | 10/2018 | Prather | G16H 10/60 |
| 2019/0209022 A1* | 7/2019 | Sobol | A61B 5/02055 |
| 2022/0189636 A1* | 6/2022 | Wagner | G06N 3/08 |
| 2024/0164688 A1 | 5/2024 | Asirvatham et al. | |

OTHER PUBLICATIONS

Wikipedia, Cross-Validation (Statistics), 2018, https://en.wikipedia.org/w/index.php?title=Cross-validation_(statistics)&oldid=870503052, 10 pages.

Xue, Y. et al., Predicting ICU Readmission Using Grouped Physiological and Medication Trends, Artificial Intelligence In Medicine, 2019, 95:27-37.

European Patent Office, Extended Search Report, Application No. 20886550.1, Oct. 20, 2023, 12 pages.

Ahmad T, et al. Machine learning methods improve prognostication, identify clinically distinct phenotypes, and detect heterogeneity in response to therapy in a large cohort of heart failure patients. J. Am. Heart Assoc. 2018;7:e008081.

Austin PC, et al. Regression trees for predicting mortality in patients with cardiovascular disease: What improvement is achieved by using ensemble-based methods? Biometrical J. 2012;54:657-673.

Bielinski SJ. Heart Failure (HF) with Differentiation between Preserved and Reduced Ejection Fraction. PheKB 2013.

Bohacik J, Kambhampati C, Davis DN, Cleland JGF. Alternating decision tree applied to risk assessment of heart failure patients. J. Inf. Technol. 2013;6:25-33.

Callender T, et al. Heart Failure Care in Low- and Middle-Income Countries: A Systematic Review and Meta-Analysis. PLoS Med 2014;11:e1001699.

CENTERS for Disease Control and Prevention, National Center for Health Statistics. 2010 National Ambulatory Medical Care Survey and 2010 National Hospital Ambulatory Medical Care Survey. Accessed online at https://www.cdc.gov/nchs/data/ahcd/namcs_summary/2010_namcs_web_tables.pdf.

Chen T, et al. XGBoost?: Reliable Large-scale Tree Boosting System. In: Conference on Knowledge Discovery and Data Mining., 2016.

Cheng JWM, et al. A review of heart failure management in the elderly population. Am. J. Geriatr. Pharmacother. 2009;7:233-249.

Fonarow GC, et al. Risk Stratification for In-Hospital Mortality in Acutely Decompensated Heart Failure: Classification and Regression Tree Analysis. JAMA 2005;293:572-580.

Fonarow GC. A review of evidence-based beta-blockers in special populations with heart failure. Rev. Cardiovasc. Med. 2008;9:84-95.

Golas SB, et al. A machine learning model to predict the risk of 30-day readmissions in patients with heart failure: a retrospective analysis of electronic medical records data. BMC Med. Inform. Decis. Mak. 2018;18:44.

Heidenreich PA, et al. Forecasting the Impact of Heart Failure in the United States. Circ. Hear. Fail. 2013;6:606-619.

Huffman MD, et al. Lifetime Risk for Heart Failure Among White and Black Americans. J. Am. Coll. Cardiol. 2013;61:1510-1517.

Klapholz M. Beta-Blocker Use for the Stages of Heart Failure. Mayo Clin. Proc. 2009;84:718-729.

Kwon J, et al. Deep learning for predicting in-hospital mortality among heart disease patients based on echocardiography. Echocardiography 2019;36:213-218.

Levy WC, et al. The Seattle Heart Failure Model: Prediction of survival in heart failure. Circulation 2006;113:1424-1433.

Modin D, et al. Influenza Vaccine in Heart Failure. Circulation 2019;139:575-586.

Mortazavi BJ, et al. Analysis of Machine Learning Techniques for Heart Failure Readmissions. Circ. Cardiovasc. Qual. Outcomes 2016;9:629-640.

NATIONAL Center for Health Statistics. Mortality Multiple Cause-of-Death Public Use Record, 2014. Available online at https://www.cdc.gov/nchs/data/dvs/Record_Layout_2014.pdf.

O'Connor CM. Bundle Up for Value-Based Heart Failure Care. JACC Hear. Fail. 2015;3:931-932.

Ortiz J, et al. One-year mortality prognosis in heart failure: a neural network approach based on echocardiographic data. J. Am. Coll. Cardiol. 1995;26:1586-93.

Panahiazar M, et al. Using EHRs and Machine Learning for Heart Failure Survival Analysis. Stud. Health Technol. Inform. 2015;216:40-44.

(56) References Cited

OTHER PUBLICATIONS

Pedregosa F, et al. Scikit-learn: Machine learning in Python. 2011.

Samad, M. D., et al. "Predicting Survival from Large Echocardiography and Electronic Health Record Datasets: Optimization with Machine Learning." JACC. Cardiovascular imaging 12.4 (2019): 681.

Schemper M, et al. A note on quantifying follow-up in studies of failure time. Control. Clin. Trials 1996;17:343-346.

Schmid FA, et al. Prognostic value of long-term blood pressure changes in patients with chronic heart failure. Eur. J. Heart Fail. 2017;19:837-842.

Shah SJ, et al. Phenomapping for Novel Classification of Heart Failure With Preserved Ejection Fraction. Circulation 2015;131:269-279.

Sprint Research Group, et al. A Randomized Trial of Intensive versus Standard Blood-Pressure Control. N. Engl. J. Med. 2015;373:2103-16.

Subramanian D, et al. New Predictive Models of Heart Failure Mortality Using Time-Series Measurements and Ensemble Models. Circ. Hear. Fail. 2011;4:456-462.

Taslimitehrani V, et al. Developing EHR-driven heart failure risk prediction models using CPXR(Log) with the probabilistic loss function. J. Biomed. Inform. 2016;60:260-269.

Tripoliti EE, et al. Heart Failure: Diagnosis, Severity Estimation and Prediction of Adverse Events Through Machine Learning Techniques. Comput. Struct. Biotechnol. J. 2017;15:26-47.

Van Buuren S et al. mice?: Multivariate Imputation by Chained Equations in R. J. Stat. Softw. 2011;45.

Ventura HO, et al. Observations on the blood pressure paradox in heart failure. Eur. J. Heart Fail. 2017;19:843-845.

Yancy CW, et al. 2017 ACC/AHA/HFSA Focused Update of the 2013 ACCF/AHA Guideline for the Management of Heart Failure. J. Am. Coll. Cardiol. 2017;70:776-803.

International Searching Authority. International Search Report and Written Opinion for application PCT/US2020/060650. Mailed on Feb. 5, 2021. 8 pages.

\* cited by examiner

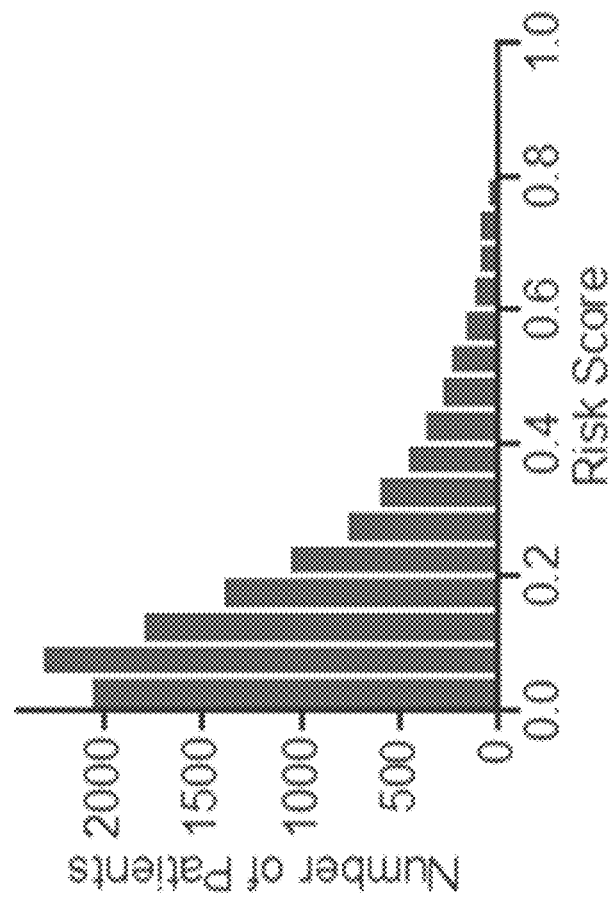
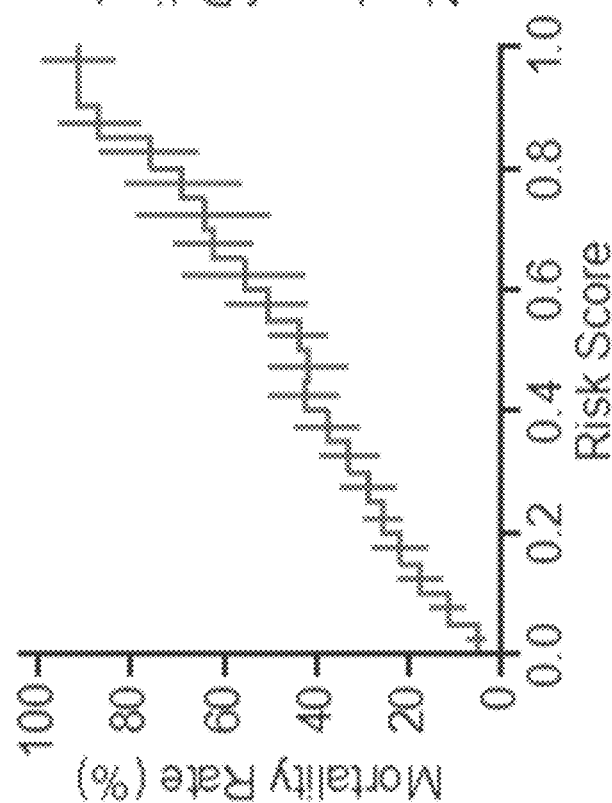
Fig. 5A
Fig. 5B

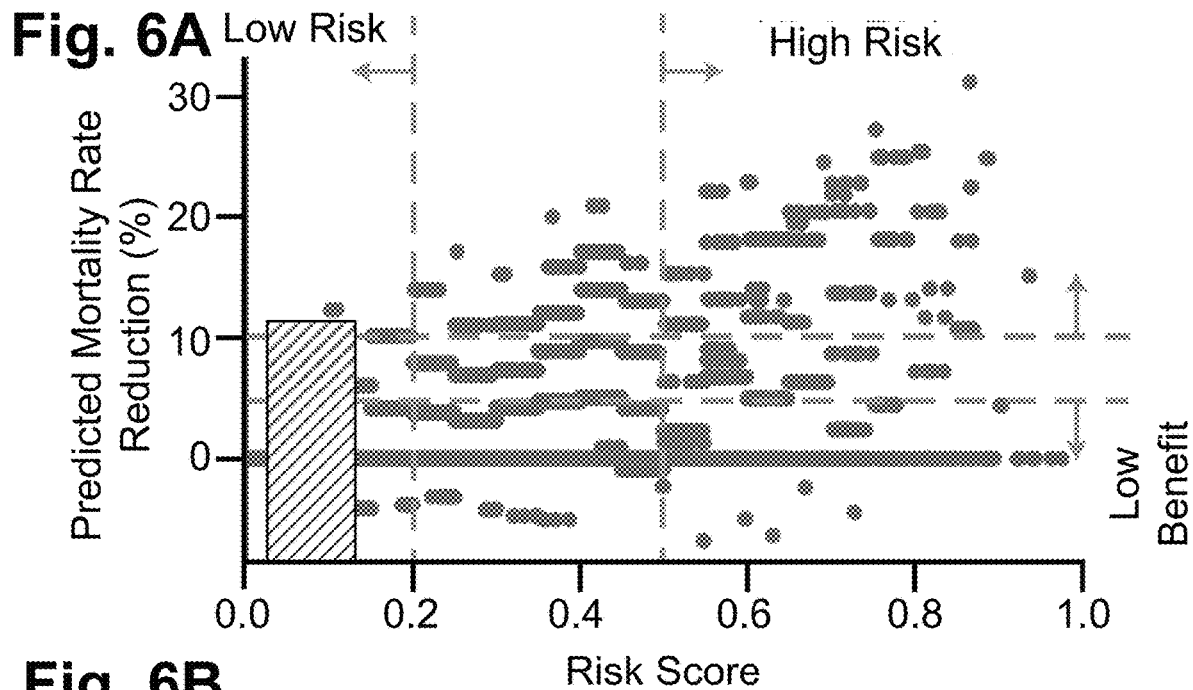
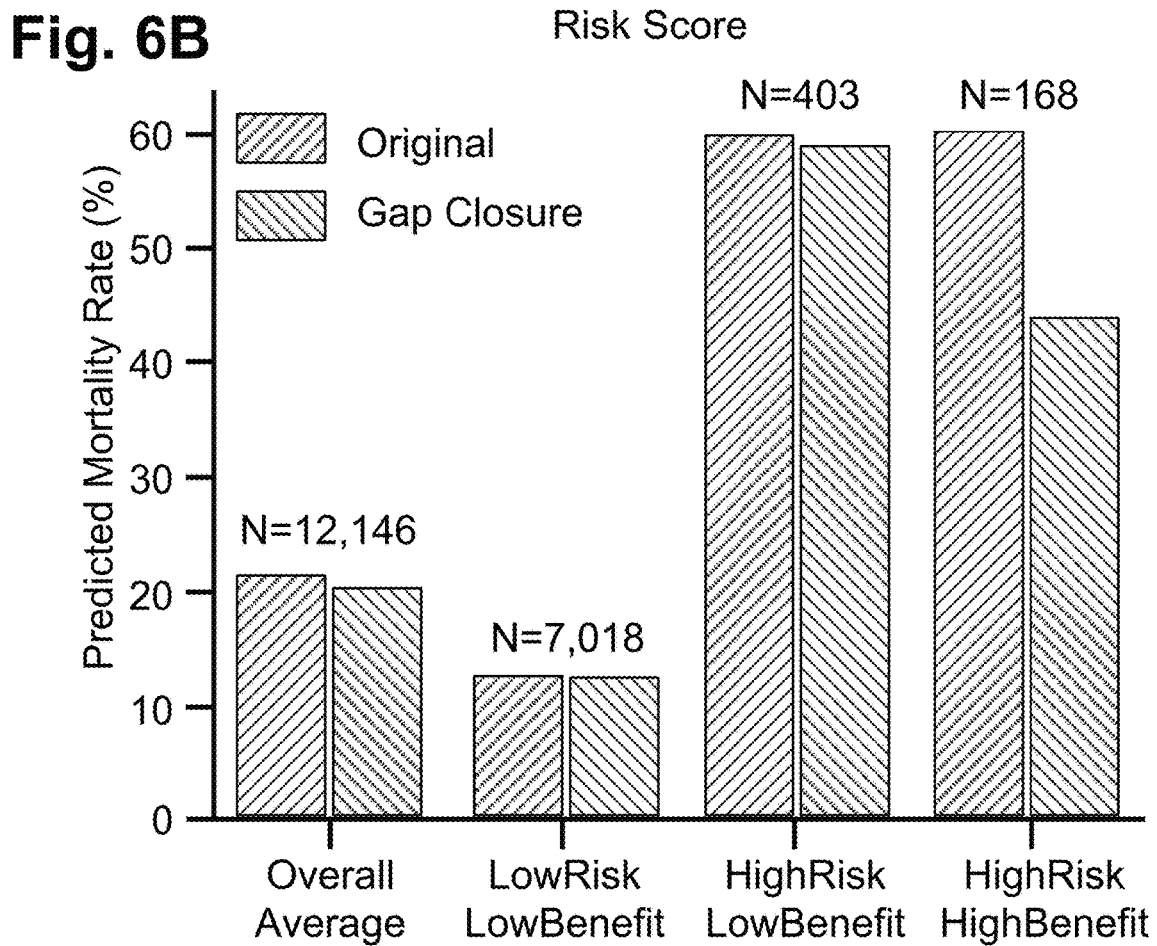

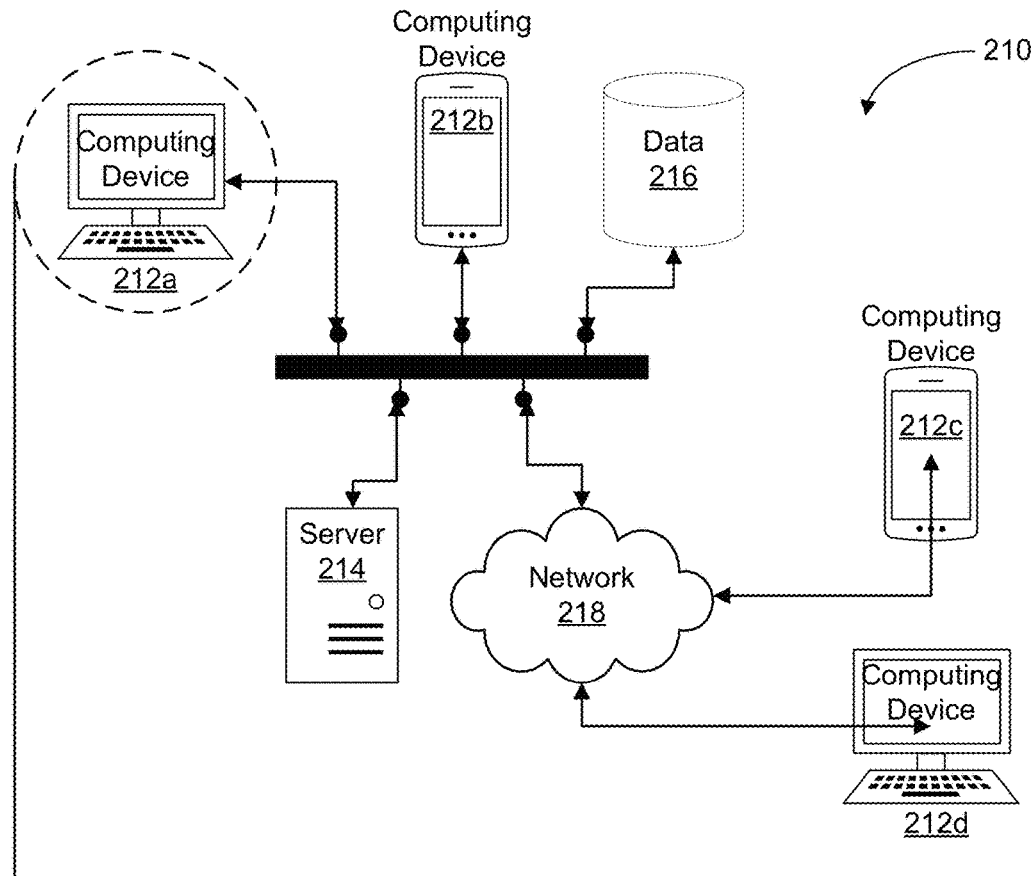
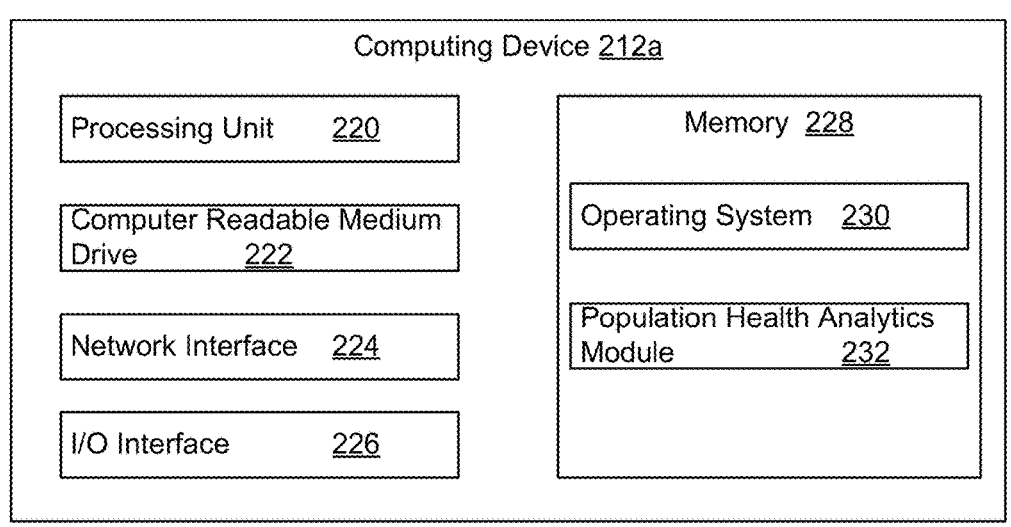
Fig. 9

SYSTEMS AND METHODS FOR MACHINE LEARNING APPROACHES TO MANAGEMENT OF HEALTHCARE POPULATIONS

CROSS-REFERENCE TO RELATED APPLICATIONS

This application is a continuation of U.S. application Ser. No. 17/098,552, filed Nov. 16, 2020, which claims the benefit of U.S. provisional application 62/936,374, filed Nov. 15, 2019.

BACKGROUND OF THE DISCLOSURE

The present invention relates to systems and methods for analysis and management of heart failure populations. Heart failure (HF) has a lifetime prevalence of 1 in 3 in the United States and is responsible for approximately 1 million hospital discharges annually and 1 in 8 deaths in the United States. The estimated annual cost of HF in the United States is $30.7 billion and that amount is expected to more than double to $69.7 billion by 2030, costing every United States citizen an average of $244 annually.

In response to these rising costs, new models of healthcare and reimbursement are being developed. In these "value-based care" models, management of many chronic conditions like heart failure is extending beyond singular patient-physician encounters to instead treat disease at a population scale. The general goal of such models is to improve patient outcomes while reducing/containing costs by delivering care that keeps patients efficiently managed and reduces the frequency of high cost/high acuity encounters. Optimizing this kind of management at a population level requires an effective means to identify and stratify patients in need of intervention and, ideally, identify appropriate interventions to deploy. At present, there is a critical lack of validated, data-driven models to support these population health goals.

Data science approaches, including machine learning, are well-suited to assist with these tasks. For example, one of the first papers on this subject in 1995 showed that a neural network could utilize echocardiography data to predict 1-year mortality in 95 heart failure patients with accuracy that was superior to a linear model or clinical judgement. Since then, numerous additional studies with thousands of patients have shown significant promise for machine learning to predict hospitalization, readmission, or death in patients with heart failure.

Previously published models using machine learning for risk predictions in patients with heart failure have two primary limitations with regard to their utility in optimizing clinical population health management. First, most models have used small, systematically collected and annotated datasets (e.g., as from a clinical trial) or focused on an important, but narrow, clinical setting (e.g., in-hospital mortality during heart failure hospitalization for acute decompensation). Such approaches, while valid and appropriate within their respective constraints, are not necessarily generalizable to a broad and heterogeneous heart failure population, as characterized in "real world" clinical data. The second limitation is that none of the published findings using machine learning models have led to clinically-relevant, actionable results.

Thus, what is needed is a system for providing clinically-relevant, actionable treatment recommendations for patients who should be but are not receiving evidence-based care generalizable to a broad and heterogeneous heart failure population.

BRIEF SUMMARY OF THE DISCLOSURE

The present disclosure includes systems and methods for machine learning approaches to management of heart failure populations. More specifically, the present disclosure provides systems and methods for providing clinically-relevant, actionable treatment recommendations for patients who should be but are not receiving evidence-based care generalizable to a broad and heterogeneous heart failure population. The present disclosure provides systems and method for generating a list of patients rank ordered by highest estimated benefit of providing additional treatments and/or other resources such as medication in order to more efficiently provide resources to patients.

Some embodiments of the present disclosure provide a method for providing treatment recommendations for a patient to a physician. The method includes receiving health information associated with the patient, determining a first risk score for the patient based on the health information using a trained predictor model, determining a second risk score for the patient based on the health information and at least one artificially closed care gap included in the health information using the predictor model, determining a predicted risk reduction score based on the first risk score and the second risk score, determining a patient classification based on the predicted risk reduction score, and outputting a report based on at least one of the first risk score, the second risk score, or the predicted risk reduction score.

To the accomplishment of the foregoing and related ends, the invention, then, comprises the features hereinafter fully described. The following description and drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE DRAWINGS

FIG. 5A is a graph of average mortality rate corresponding to risk score bin data derived from training data across all training years.

FIG. 5B is a graph of a distribution of predicted risk score in a prediction set (alive patients), which was then translated to predicted mortality rate using the relationship shown in FIG. 5A.

FIG. 6A is a scatter plot of risk score and corresponding benefit for individual patients in a prediction set.

FIG. 6B is a graph of average mortality rate before and after care gap closure simulation in selected groups.

FIG. 9 is an exemplary system for implementing the process of FIG. 8.

Figure 1:
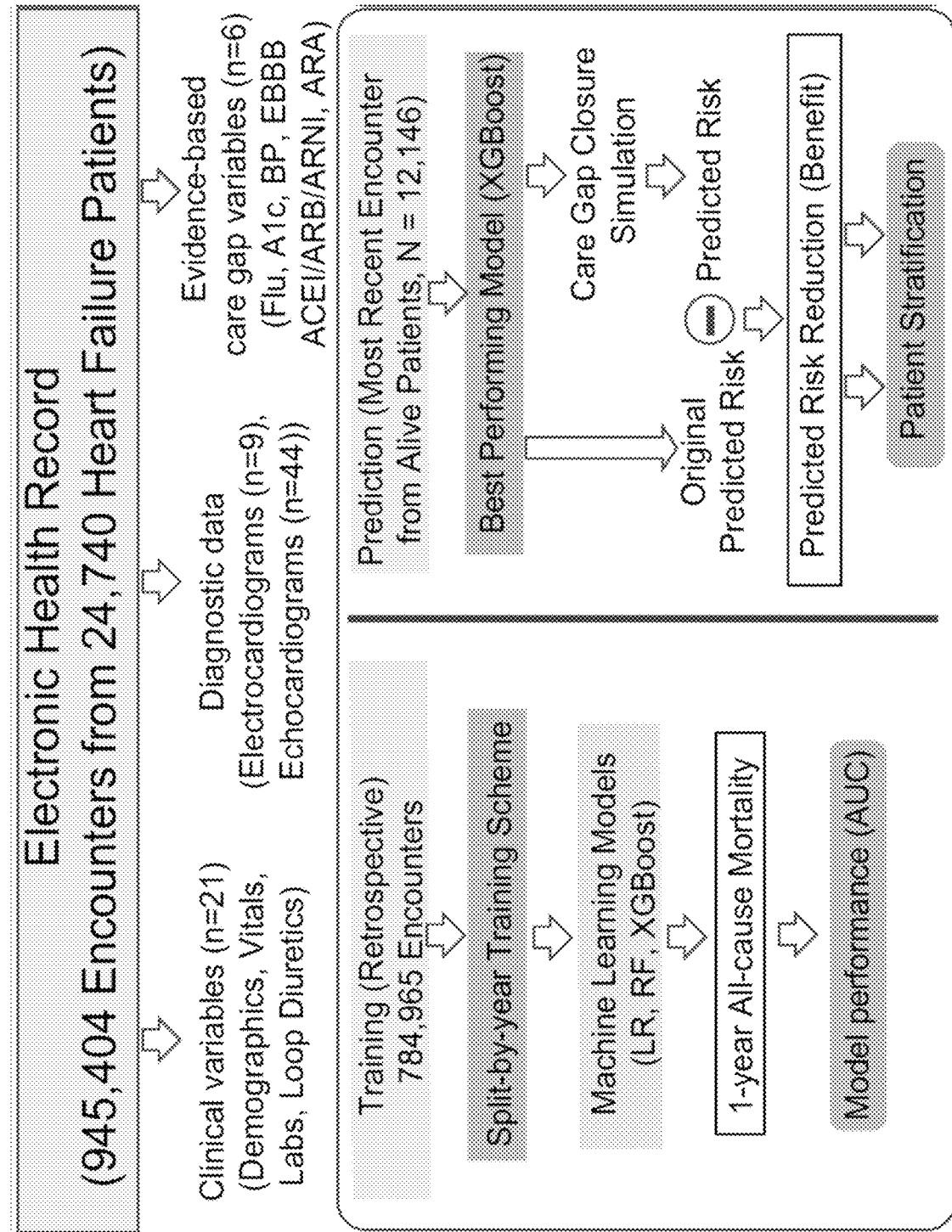
FIG. 1 is a flow for training models for predicting 1-year all-cause mortality using electronic health record (EHR) data and predicting mortality risk with and without artificially closing care gaps.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE DISCLOSURE

The various aspects of the subject invention are now described with reference to the annexed drawings. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, clinical trial designers, oncologists, neurologists, psychiatrists, data scientists, and many other persons with specialized skill sets.

The term "physician" will be used to refer generally to any health care provider including but not limited to a primary care physician, a medical specialist, an oncologist, a neurologist, a nurse, and a medical assistant, among others.

The term "researcher" will be used to refer generally to any person that performs research including but not limited to a radiologist, a data scientist, or other health care provider. One person may be both a physician and a researcher while others may simply operate in one of those capacities.

Furthermore, the disclosed subject matter may be implemented as a system, method, apparatus, or article of manufacture using programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (such as hard disk, floppy disk, magnetic strips), optical disks (such as compact disk (CD), digital versatile disk (DVD)), smart cards, and flash memory devices (such as card, stick). Additionally it should be appreciated that a carrier wave can be employed to carry computer-readable electronic data such as those used in transmitting and receiving electronic mail or in accessing a network such as the Internet or a local area network (LAN). Transitory computer-readable media (carrier wave and signal based) should be considered separately from non-transitory computer-readable media such as those described above. Of course, those skilled in the art will recognize many modifications may be made to this configuration without departing from the scope or spirit of the claimed subject matter.

In this disclosure, ARB refers to angiotensin II receptor blocker, ACEI refers to active angiotensin-converting enzyme inhibitor, ARA refers to aldosterone receptor antagonist, ARNI refers to angiotensin receptor-neprilysin inhibitor, AUC refers to area under the receiver operating characteristic curve, EBBB refers to evidence-based beta-blocker, ECG refers to electrocardiogram, and EHR refers to electronic health record.

The inventors leveraged a large 20-year retrospective dataset derived from a health system (Geisinger) that was an early adopter of electronic health record (EHR) technology to develop a predictive model for all patients with heart failure using machine learning. This model included a comprehensive set of input variables, including 6 "care gap" indicators. A "Care Gap" is defined as the discrepancy between recommended best practices and the care that is actually provided.

Importantly, this novel incorporation of evidence-based care gaps into a predictive model represents a methodology for driving clinical action from a machine learning model (not just predicting risk but predicting reduction in risk, or "benefit", as a result of action). Moreover, it is demonstrated how such insights might be utilized through population health management efforts to simultaneously stratify risk and therapeutic benefit at an individual patient level to efficiently deploy healthcare resources.

Methods

EHR Data Collection

Patients with heart failure over a 19 year period (January 2001-February 2019) were identified from Geisinger EHRs. Heart failure was defined using the validated eMERGE phenotype. All clinical encounters since 6 months prior to the heart failure diagnosis date, including outpatient office visits, hospital admissions, emergency room visits, lab tests and cardiac diagnostic studies (e.g. echocardiograms or electrocardiograms), were identified as independent samples.

Model Inputs

FIG. 1 is a flow for training models for predicting 1-year all-cause mortality using EHR data and predicting mortality risk with and without simulating care gap closure/treatment by artificially closing care gaps. 1-year all-cause mortality was studied in a large cohort of heart failure patients using machine learning models to integrate clinical variables, measures from diagnostic studies (e.g. echocardiography and electrocardiography) and evidence-based care gap variables from electronic health records. Mean area under the ROC curve (AUC) from a 'split-by-year' training scheme was reported to evaluate model performance. The best performing model was then used to estimate risk reduction (potential benefit) by artificially closing care gaps in a prospective prediction set and to evaluate the efficiency of benefit-driven patient prioritization. FIG. 1 identifies various exemplary machine learning models that may be used as part of this process, including logistic regression ("LR"), random forest ("RF"), and XGBoost. Within FIG. 1, the abbreviation BP indicates blood pressure.

A total of 80 variables were collected from the EHR (see FIG. 1): 8 clinical variables (age, sex, height, weight, smoking status, heart rate, systolic and diastolic blood pressures), use of loop diuretics, 12 biomarkers (hemoglobin, eGFR, CKMB, lymphocytes, HDL, LDL, uric acid, sodium, potassium, NT-proBNP, troponin T, A1c), 44 non-redundant echocardiographic variables, 9 ECG measurements (such as QRS duration) and 6 care gap variables (described below). Lab values, vital signs and ECG measures closest to the encounter date within a 6-month window were extracted. All echocardiographic measurements recorded in the Xcelera database within 12 months of the encounter date were extracted. If no measurements were available within the specified time window, the variable was set to missing. EHR data preprocessing and cleaning is further detailed in the "EHR Data Preprocessing" section below. It is understood that these variables are just one of many possible collections of variables that could be used to train similar models. Moreover, additional data types such as medical image data, medical signals data (e.g. electrocardiograms), genomic data, etc., can be used as inputs to the model.

EHR Data Preprocessing

Physiologic limits for echocardiographic variables were defined with assistance from a cardiologist with expertise in echocardiography. Data cleaning included removal of 1) redundant variables that were derived directly from other variables and 2) values outside physiologically possible ranges as defined by a cardiologist, including physiologically impossible values likely due to human error (e.g. LVEF <0% or >100%, height and weight below 0). The removed values were then set as missing.

Since the predictive models require complete datasets, missing data for continuous variables were imputed using two steps. First, missing values in between encounters for an individual patient were linearly interpolated if complete values were found in the adjacent encounters. Next, measurements that were missing in 90% or more samples were discarded to ensure enough samples are available for imputation for each measurement, and the remaining missing values were imputed using a robust Multivariate Imputation by Chained Equations (MICE).

Missing values for diastolic function (represented as a categorical variable), were imputed by training a One-vs-All logistic regression classifier from all samples where diastolic function was available. Diastolic function was reported as an ordinal variable based on level of abnormality, with −1 for normal, 0 for abnormal (no grade reported), and 1, 2 or 3 for grades I, II and III diastolic dysfunction, respectively.

Care Gap Variables

Six evidence-based, actionable interventions (care gap variables) were introduced to the machine learning models to study their association with patient outcomes: 1) flu vaccine administration, 2) hemoglobin A1c in goal (<8%), 3) BP in goal (blood pressure <140/90 mmHg), 4) active evidence-based beta-blocker (EBBB), 5) active angiotensin-converting enzyme inhibitor (ACEI), angiotensin II receptor blocker (ARB) or angiotensin receptor-neprilysin inhibitor (ARNI) and 6) active aldosterone receptor antagonist (ARA). These care gap variables were defined with assistance from a cardiologist and a pharmacist with heart failure expertise. Detailed inclusion/exclusion criteria are listed in Table 1 below. A blinded chart review validation of each care gap variable is detailed in the "Care Gap Validation" section below. It is understood that there are treatments or interventions other than the listed care gap variables that can be input to the model, for example medications, clinic visits, provider visits to the patient home, etc. Note that for new therapies or medications for which outcomes have not yet been acquired in a large retrospective clinical dataset to facilitate the most accurate machine learning model training, data showing the effect of a therapy on a particular outcome of interest can be used until enough data is captured to generate a new model.

TABLE 1

| Care Gap Definitions | | | |
| --- | --- | --- | --- |
| Care Gap | Inclusion | Exclusion | Gap Closure |
| Flu vaccine | N/A | Allergy | Received flu vaccine in the current flu season |
| Blood pressure (BP) in goal | N/A | N/A | Open (not in goal) if >=2 of the 5 most recent readings in the past 12 months are >140 for systolic or >90 for diastolic |
| A1c in goal | Diagnosis of diabetes (defined using problem list diagnoses) | N/A | Most recent A1c within the last 6 months <8% |

TABLE 1-continued

Care Gap Definitions

| Care Gap | Inclusion | Exclusion | Gap Closure |
|---|---|---|---|
| Evidence- based beta-blocker (EBBB) | Diagnosis of heart failure with most recent left ventricular ejection fraction (LVEF) <40% | Bradycardia (heart rate <60 by averaging up to 5 most recent readings in last 6 months) On inotropic therapy History of $2^{nd}$ or $3^{rd}$ degree heart block without ICD or pacemaker Hypotension (systolic pressure < 100 mmHg by averaging last 5 readings in past 6 months) Severe chronic obstructive pulmonary disease (COPD) or asthma Allergy or contraindications | Currently taking EBBB |
| Active angiotensin-converting enzyme inhibitor (ACEI)/ Angiotensin II receptor blocker (ARB)/ Angiotensin receptor-nepri lysin inhibitor (ARNI) | Diagnosis of heart failure with most recent LVEF <40% | Pregnancy History of angioedema Hypotension Serum creatinine >2 in any of preceding 3 measurements Potassium >5 in any of previous 3 measurements Allergy or contraindications Newly initiated dialysis | Currently taking ACEI or ARB or ARNI |
| Aldosterone receptor antagonist (ARA) | Diagnosis of heart failure with most recent LVEF <35% | Hypotension Serum creatinine >2 in any of preceding 3 measurements Potassium >5 in any of preceding 3 measurements On dialysis Allergy or contraindications | Currently taking ARA |

Care Gap Validation

To validate the accuracy of the defined care gap variables, two reviewers independently and manually reviewed 50-100 charts for each care gap variable in blinded fashion. Specifically, a questionnaire was created in REDCap for each care gap variable, with questions covering patient inclusion (e.g. if patient has heart failure), gap open/closed status (e.g., if patient's most recent A1C was <8%), and exclusion criteria (e.g., if patient is allergic to flu vaccine). 50-100 cases were randomly selected for each care gap from our database while balancing positive and negative cases for each criterion. For example, for flu vaccine, 25 cases had an expected open gap (no flu vaccine received) and 25 with an expected closed gap (flu vaccine received). The number of cases was determined based on how many criteria/questions were included for each care gap. Note that since there were multiple exclusion criteria involved for the medication related gaps with rare frequency in the EHR, we did not balance the cases based on exclusion criteria, but only ensured that representative cases were included. For the selected cases, patients' medical record number (MRN, unique identifier) and encounter dates were provided to the reviewer. The reviewer then filled out the questionnaire by reviewing the patient's chart in EPIC, using the provided encounter dates as the reference date. This was used as the ground truth to compare with our calculated care gap data. A summary of the review results is presented in Table 2 below. In Table 2, N/A means there are no inclusion/exclusion restrictions for the gap.

TABLE 2

| | Cases | Accuracy (%) | | |
|---|---|---|---|---|
| | Reviewed (N) | Inclusion | Open/Closed | Exclusion |
| ACEI/ARB/ARNI | 100 | 93 | 98 | 99 |
| Aldosterone receptor antagonist | 100 | 94 | 99 | 97 |
| BP in goal | 50 | N/A | 98 | N/A |
| A1c in goal | 50 | 90 | 100 | N/A |
| Evidence-based beta-blocker | 100 | 88 | 98 | 94 |
| Flu vaccine | 50 | N/A | 100 | 100 |

Primary Outcome

Machine learning models were used to predict all-cause mortality 1 year after the associated encounter date. Survival duration was calculated from the date of death (cross-referenced with national death index databases on a monthly basis) or last known living encounter from the EHR. It is understood that this is an example of a single clinically relevant endpoint, however, additional endpoints include but are not limited to hospital admissions, emergency department or clinic visits, total cost of care, adverse outcomes such as stroke or heart attack, etc.

Machine Learning Model Training and Evaluation

First, a linear logistic regression classifier was used for its simplicity (particularly for examining directionality of associations between model inputs and the primary outcome), and then compared to the performance to non-linear models including random forest and XGBoost (a scalable gradient tree boosting system). These nonlinear models were hypothesized to improve predictive accuracy by capturing more complex, non-linear relationships among input variables. The best performing model was selected for subsequent analysis of care gap closure effect estimation. Models were evaluated using a 'split-by-year' form of cross-validation as described in the "Machine Learning Model Evaluation" section below.

Machine Learning Model Evaluation

The most recent encounters were excluded in all alive patients with heart failure (as of Feb. 9, 2019) as a prospective, prediction dataset (a clinically "actionable" dataset). All remaining samples (encounters) with known outcome status were used for model evaluation.

To evaluate the proposed model, the inventors deviated from the traditional cross-validation approach, because the random split approach misrepresents the "real-world" deployment scenario. Instead a 'split-by-year' procedure was followed to divide the samples into training (past) and test sets (future). To deploy a model, the model is trained on all available data prior to the present date and applied to the patient's most recent encounter, therefore, one can retrospectively evaluate the model as if it were deployed in a given date. For each year (e.g. 2010), the cutoff date was set as January $1^{st}$ of that year (Jan. 1, 2010) such that all encounters prior to the cutoff date were used for training, and the first encounter for a given patient after the cutoff (but within the calendar year, from Jan. 1, 2010-Dec. 31, 2010) was used for testing. This process was repeated for years 2010-2018.

Area under the receiver operating characteristic (ROC) curve (AUC) from the test set was obtained and overall model performance was reported as the mean AUC and standard deviation over all training years. The average importance and ranking for each individual variable over all training years was obtained to identify the most important variables. The open source python packages "scikit-learn" (version 0.20.0) and "xgboost" (version 0.80) were used to implement the machine learning pipeline and evaluate the models.

After the training stage, an optimal set of hyper-parameters was obtained, and further used to re-train the entire dataset to obtain a final model. The final model was then used on the held out actionable prediction dataset (most recent encounters from all patients alive as of Feb. 9, 2019) to obtain a likelihood score for each individual patient. This likelihood score, which is referred as the risk score, ranged from 0 to 1, with higher values corresponding to higher risk of mortality.

During training, a risk score was obtained for each individual sample in the test set. These risk scores were binned into 20 groups of 0.05 increments from 0-1, and the true mortality rate was calculated using ground truth from samples within that group. The average event rate over all training years for a specific bin was used to estimate the event rate as a function of the computed risk scores in the prediction set. This enabled a mapping of risk scores to the mortality event rate.

Benefit Prediction in Alive Patients by Simulation of Care Gap Closure

To study the effect of closing care gaps on improving patient outcomes, care gaps were artificially closed (i.e. changing the value from 1=open/untreated to 0=closed/treated) while keeping all other variables unchanged. A care gap was not closed in patients who met the exclusion criteria for that care gap (for example, a patient with bradycardia who could not be treated with EBBB). First, a logistic regression was used to estimate the associated directionality of each care gap variable with the predicted mortality risk (e.g. receiving flu vaccine associated with decreased mortality risk). No care gaps that had a negative or undetermined relationship with the outcome (i.e. BP in goal, as described later) were closed. For care gaps which had a positive relationship with the outcome, the gap closure was simulated in the best performing non-linear model by artificially closing the gap and re-calculating the risk score using the same model.

After the simulation, the change in risk score, i.e., the difference between baseline risk score with care gaps open and risk score with care gaps closed, was calculated for each patient, which was further translated into an estimated benefit, i.e. reduction in estimated mortality rate. The cumulative sum of the benefit from all patients was then used to provide an estimated number of lives that could be saved by closing care gaps. In some embodiments, the risk score with care gaps open and/or the risk score with care gaps closed can be provided to and used by a physician and/or a provider to estimate the risk of death of a specific patient. In this way, the physician and/or provider can estimate if the patient has a high likelihood of dying within the year (or other time period) so that appropriate resources such as palliative care physicians can be provided to the patient at an appropriate time.

Results

Study Population 24,740 patients with heart failure who collectively had 945,404 encounters (median age 76 years, 45% female) within the EHRs that fit the inclusion criteria were identified. Note that while encounters are used as a prediction input to the models in this scenario, the prediction input can be configured differently for example by using "episodes" where multiple encounters are concatenated or otherwise combined into one point in time from which the prediction is made. Tables 3 and 4 below show summary statistics. On average, each patient had 38 encounters (interquartile range (IQR): 10-49). The median follow up duration was 3.4 years (IQR: 1.4-6.3 years) using reverse Kaplan-Meier, and 12,594 (51%) had a recorded death. Data are reported as median [interquartile range], or percentage.

TABLE 3

Basic Demographics and Patient Characteristics.

| | All (N = 945,404 encounters from 24,740 patients) | Most recent encounter from alive patients (N = 12,416) |
|---|---|---|
| Age (yr) | 76 [67-83] | 75 [65-84] |
| Male (%) | 55 | 53 |
| Smoking History (current or ever smoking) (%) | 64 | 62 |
| Height (cm) | 168 [157-175] | 168[159-175] |
| Weight (kg) | 85 [70-102] | 86 [72-105] |
| Diastolic Pressure (mmHg) | 68 [60-74] | 70 [61-78] |
| Systolic Pressure (mmHg) | 124 [112-137] | 124 [112-138] |
| Heart Rate (bpm) | 72 [64-80] | 73 [64-82] |
| Ejection Fraction (%) | 52 [37-57] | 52 [40-57] |
| High-density lipoprotein (HDL) (mg/dL) | 45 [36-54] | 45 [38-52] |
| Low-density lipoprotein (LDL) (mg/dL) | 80 [61-101] | 83 [64-100] |
| N-terminal-pro B-type natriuretic peptide (NT-proBNP) (pg/mL) | 3264 [1054-6129] | 2960 [869-5443] |
| Troponin T (ng/mL) | 0.02 [0.01-0.09] | 0.03 [0.01-0.14] |

TABLE 4

| All encounters (N=945,404) | Percentage/Median [IQR] | Description |
|---|---|---|
| Age (years) | 76 [67-83] | |
| Sex (% male) | 55% | |
| Smoking status (% smoker) | 64% | |
| Height (cm) | 168 [157-175] | |
| Weight (kg) | 85 [70-102] | |
| Heart rate (bpm) | 72 [64-80] | |
| Diastolic blood pressure (mmHg) | 68 [60-74] | |
| Systolic blood pressure (mmHg) | 124 [112-137] | |
| LDL (mg/DL) | 80 [61-101] | Low-density lipoprotein |
| HDL (mg/DL) | 45 [36-54] | High-density lipoprotein |
| A1c (%) | 6.4 [5.8-7.1] | |
| CKMB (ng/mL) | 3.4 [2.2-6.1] | Creatine kinase-muscle/brain |
| Hemoglobin (g/dL) | 12.3 [10.9-13.6] | |
| Lymphocytes (%) | 19 [12-25] | |
| Potassium (mmol/L) | 4.3 [4.0-4.6] | |
| NT-proBNP (pg/mL) | 3264 [1054-6129] | N-terminal-pro hormone B-type natriuretic peptide |
| Sodium (mmol/L) | 140 [137-142] | |
| Troponin T (ng/mL) | 0.02 [0.01-0.09] | |
| eGFR (mL/min/1.73^m2) | 52.5 [37.3-60] | Estimated glomerular filtration rate |
| Uric acid (mg/dL) | 7.0 [6.4-7.6] | Urate in serum or plasma |
| Loop diuretics (% taking) | 62% | |
| QRS duration (ms) | 106 [90-138] | |
| QT (ms) | 418 [382-454] | QT interval |
| QTc (ms) | 462 [436-492] | QT interval corrected for heart rate |
| PR interval (ms) | 174 [150-204] | |
| Vent rate (bpm) | 74 [64-86] | Ventricular rate |
| RR interval (ms) | 814 [694-936] | Average RR interval |
| P axis (degree) | 53 [38-66] | |
| R axis (degree) | 10 [−30-56] | |
| T axis (degree) | 66 [27-104] | |
| LVEF (%) | 52 [37-57] | Physician-reported left ventricular ejection fraction |
| AI dec slope (cm/s2) | 219 [204-234] | Aortic insufficiency deceleration slope |
| AI max vel (cm/s) | 359 [348-369] | Aortic insufficiency maximum velocity |
| Ao V2 VTI (cm) | 36 [31-42] | Velocity-time integral of distal to aortic valve flow |
| Ao V2 max (cm/s) | 152 [122-191] | Maximum velocity of distal to aortic valve flow |
| Ao root diam (cm) | 3.2 [3.0-3.5] | Aortic root diameter |
| Asc Aorta (cm) | 3.3 [3.1-3.5] | Ascending aorta diameter |
| EDV (MOD*-sp2) (ml) | 113 [94-135] | LV end-diastolic volume: apical 2-chamber |
| EDV (MOD*-sp4) (ml) | 114 [94-137] | LV end-diastolic volume: apical 4-chamber |
| EDV (sp2-el**) | 117 [98-140] | LV end-diastolic volume: apical 2-chamber |
| EDV (sp4-el**) | 118 [98-143] | LV end-diastolic volume: apical 4-chamber |
| ESV (MOD*-sp2) (ml) | 61 [45-80] | LV end-systolic volume: apical 2-chamber |
| ESV (MOD*-sp4) (ml) | 63 [46-81] | LV end-systolic volume: apical 4-chamber |
| ESV (sp2-el**) (ml) | 63 [47-83] | LV end-systolic volume: apical 2-chamber |
| ESV (sp4-el**) (ml) | 66 [50-85] | LV end-systolic volume: apical 4-chamber |
| IVSd (cm) | 1.2 [1.0-1.3] | IV septum dimension at end-diastole |
| LA dimension (cm) | 4.3 [3.8-4.8] | Left atrium dimension |
| LAV (MOD*-sp2) (ml) | 75 [64-85] | Left atrium volume: apical 2-chamber |
| LAV (MOD*-sp4) (ml) | 75 [63-85] | Left atrium volume: apical 4-chamber |
| LV V1 VTI (cm) | 19 [17-21] | Velocity-time integral: proximal to the obstruction |
| LV V1 max (cm/s) | 90 [76-104] | Maximum LV velocity: proximal to the obstruction |
| LVIDd (cm) | 5.0 [4.4-5.6] | LV internal dimension at end-diastole |
| LVIDs (cm) | 3.6 [3.0-4.2] | LV internal dimension at end-systole |
| LVLd ap2 (cm) | 8.1 [7.8-8.6] | LV long-axis length at end diastole: apical 2-chamber |
| LVLd ap4 (cm) | 8.1 [7.7-8.6] | LV long-axis length at end diastole: apical 4-chamber |

TABLE 4-continued

| All encounters (N=945,404) | Percentage/Median [IQR] | Description |
| --- | --- | --- |
| LVLs ap2 (cm) | 7.2 [6.8-7.7] | LV long-axis length at end systole: apical 2-chamber |
| LVLs ap4 (cm) | 7.2 [6.8-7.7] | LV long-axis length at end systole: apical 4-chamber |
| LVOT area (M) (cm2) | 3.4 [3.2-3.6] | LV outflow tract area |
| LVOT diam (cm) | 2.1 [2.0-2.2] | LV outflow tract diameter |
| LVPWd (cm) | 1.1 [1.0-1.3] | LV posterior wall thickness at end-diastole |
| MR max vel (cm/s) | 482 [466-498] | Mitral regurgitation maximum velocity |
| MV A point (cm/s) | 79 [64-92] | A-point maximum velocity of mitral flow |
| MV E point (cm/s) | 94 [74-115] | E-point maximum velocity of mitral flow |
| MV P1/2t max vel (cm/s) | 115 [100-128] | Maximum velocity of mitral valve flow |
| MV dec slope (cm/s2) | 497 [409-567] | Mitral valve deceleration slope |
| MV dec time (s) | 0.20 [0.17-0.24] | Mitral valve deceleration time |
| PA V2 max (cm/s) | 95 [85-102] | Maximum velocity of distal to pulmonic valve flow |
| PA acc slope (cm/s2) | 689 [533-821] | Pulmonary artery acceleration slope |
| PA acc time (s) | 0.10 [0.08-0.12] | Pulmonary artery acceleration time |
| Pulm. R-R (s) | 0.86 [0.83-0.90] | Pulmonary R-R time interval |
| RAP systole (mm-Hg) | 8.0 [7.1-8.8] | Right atrial end-systolic mean pressure |
| RVDd (cm) | 3.5 [3.3-3.6] | Right ventricle dimension at end-diastole |
| TR max vel (cm/s) | 275 [248-303] | Tricuspid regurgitation maximum velocity |
| Diastolic function (severity: %) | −1: 12%<br>0: 29%<br>1: 31%<br>2: 17%<br>3: 11% | −1: normal;<br>0: abnormal (no grade reported);<br>1: grade 1 dysfunction;<br>2: grade II dysfunction;<br>3: grade III dysfunction |
| ACEI/ARB/ARNI (% open) | 9%[1] | See Table 1 |
| Aldosterone receptor antagonist (% open) | 14% | See Table 1 |
| BP in goal (% open) | 23% | See Table 1 |
| A1c in goal (% open) | 26% | See Table 1 |
| Evidence-based beta-blocker (% open) | 7% | See Table 1 |
| Flu vaccine (% open) | 39% | See Table 1 |

Figure 2:
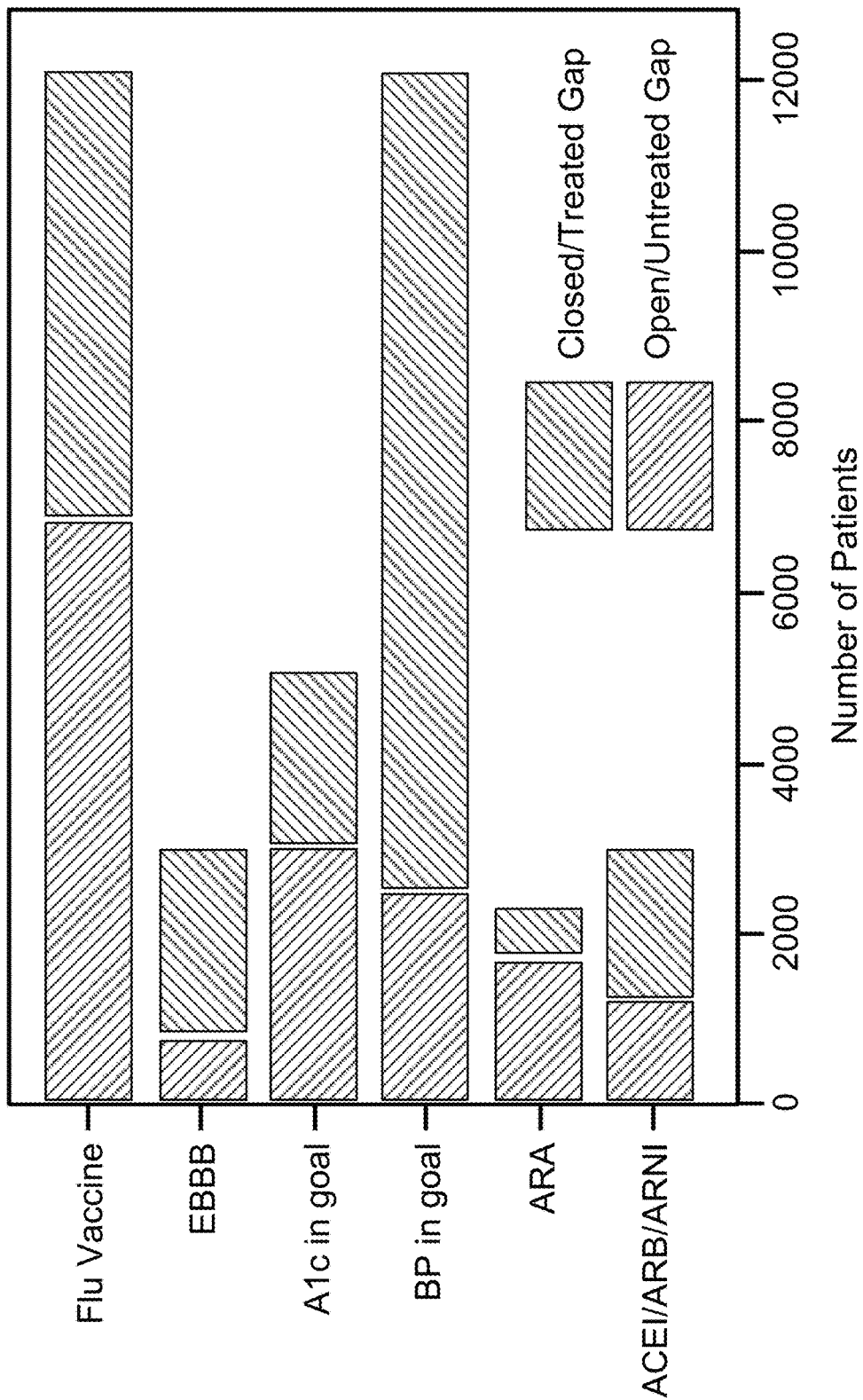
FIG. 2 is a graph of the number of patients for each gap for which the gap was open/untreated or closed/treated.

Of the 12,146 patients who were alive as of Feb. 2, 2019, 9,474, (78%) had at least one open care gap, and 501 (4%) had 4 or more care gaps open as of their most recent encounter dates. FIG. 2 is a graph of the number of patients for each gap for which the gap was open/untreated or closed/treated. The sum of those groups represents the number of patients who were eligible for the gap (i.e., who fit the inclusion criteria). Depending on the gap, 20-74% of eligible patients had an open gap. Additional details are available in Table 5 below. In Table 5, percentage of exclusion and percentage of open are calculated based on number of included encounters (i.e., encounters during which a patient was eligible and thus satisfied the inclusion criteria for taking the medicine). In FIG. 2, EBBB (also mentioned in FIG. 1) stands for evidence-based beta-blocker, ACEI stands for active angiotensin-converting enzyme inhibitor, ARB stands for angiotensin II receptor blocker, ARNI stands for angiotensin receptor-neprilysin inhibitor, and ARA stands for aldosterone receptor antagonist.

TABLE 5

| | Training set (N = 784,965) | | | Prediction set (N = 12,146) | | |
| --- | --- | --- | --- | --- | --- | --- |
| | Inclusion | Exclusion | Gap Open | Inclusion | Exclusion | Gap Open |
| ACEI/ARB/ARNI | 183,918 (23%) | 37,508 (20%) | 72,943 (40%) | 2,991 (25%) | 447 (15%) | 1,219 (41%) |
| Aldosterone receptor antagonist | 145,098 (18%) | 38,421 (26%) | 111,326 (77%) | 2,301 (19%) | 500 (22%) | 1,712 (74%) |

TABLE 5-continued

| | Training set (N = 784,965) | | | Prediction set (N = 12,146) | | |
|---|---|---|---|---|---|---|
| | Inclusion | Exclusion | Gap Open | Inclusion | Exclusion | Gap Open |
| BP in goal | 784,965 (100%) | 0 (0%) | 176,330 (22%) | 12,146 (100%) | 0 (0%) | 2,473 (20%) |
| A1c in goal | 372,774 (47%) | 0 (0%) | 201,881 (54%) | 5,088 (42%) | 0 (0%) | 3,010 (59%) |
| Evidence-based beta-blocker | 183,918 (23%) | 9,734 (5%) | 183,918 (34%) | 2991 (25%) | 104 (3%) | 780 (26%) |
| Flu vaccine | 784,965 (100%) | 11,353 (1%) | 300,368 (38%) | 12,146 (100%) | 177 (1%) | 6,849 (56%) |

Accuracy for Predicting all-Cause Mortality Using Machine Learning

Figures 3A, 3B:
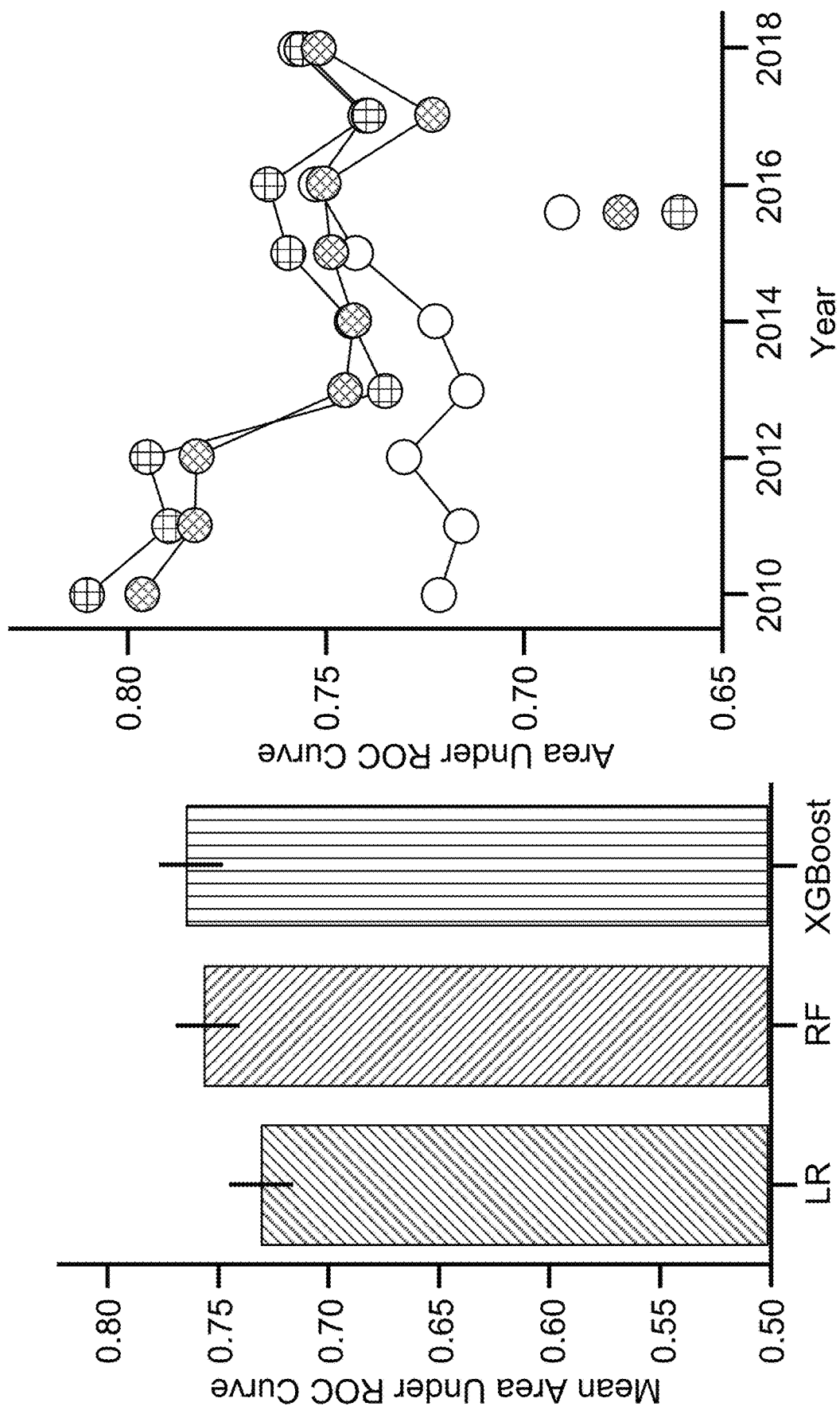
FIG. 3A is a graph of mean area-under-curve for linear and non-linear models.
FIG. 3B is a graph of area under curve for years 2010-2018 for the linear and non-linear models.

All three machine learning models predicted 1-year all-cause mortality with AUCs above 0.70, and the non-linear models achieved higher average AUCs (random forest: 0.76±0.02, XGBoost: 0.77±0.03) compared to linear logistic regression (0.73±0.02; FIG. 3). FIG. 3A is a graph of mean AUC for linear and non-linear models. Both non-linear models performed better than linear logistic regression (LR) at predicting 1-year all-cause mortality, with XGBoost (XGB) having the highest average AUC. FIG. 3B is a graph of area under curve for years 2010-2018 for linear and non-linear models.

Figure 4:
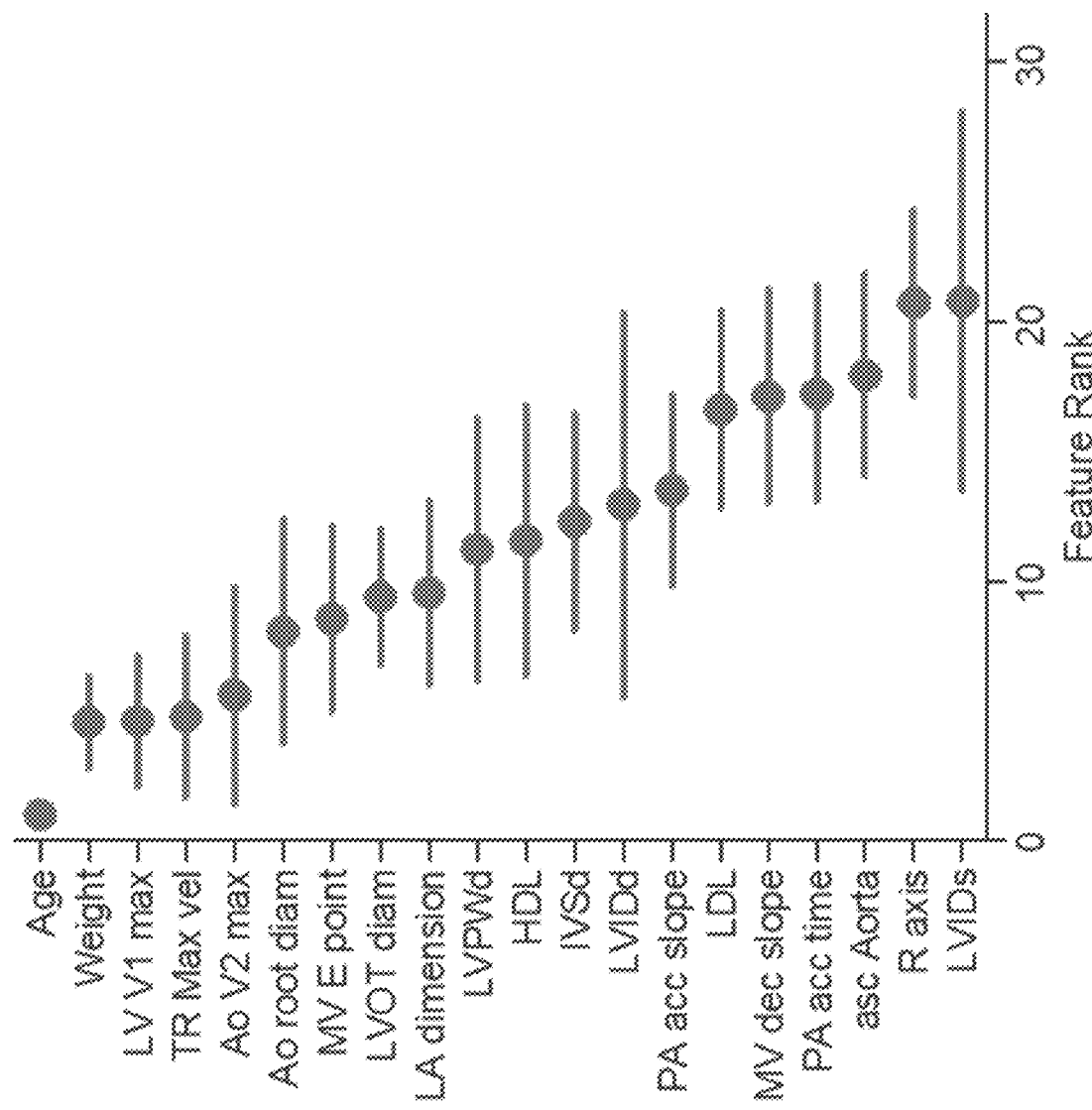
FIG. 4 is a graph of the top twenty ranking variables using XGBoost.

FIG. 4 is a graph of the top twenty ranking variables using XGBoost. Besides commonly used clinical variables (age, weight) and biomarkers (HDL, LDL), echocardiographic variables are highly important for predicting 1-year all-cause mortality in patients with heart failure. See Table 4 above for variable descriptions. Variable importance rankings using XGBoost demonstrated that 15 of the top 20 variables were echocardiographic measures. Logistic regression results demonstrated that 5 of the 6 care gap variables (all but BP in goal) had an expected positive association such that an open gap was associated with higher risk of 1-year all-cause mortality. Only these 5 variables were used to predict the effect of closing care gaps in subsequent models.

Predicting Benefit of Closing Care Gaps

XGBoost was chosen as the final model to predict the benefit of closing care gaps in the alive patients, since the XGBoost model had the highest AUC in the retrospective data. The distribution of risk scores is shown in FIGS. 5A-B. FIG. 5A is a graph of average mortality rate corresponding to each risk score bin derived from the training data across all training years. FIG. 5B is a graph of a distribution of predicted risk score in the prediction set (alive patients), which was then translated to predicted mortality rate using the relationship shown in FIG. 5A. The number of encounters included in each training/test fold per year is included in Table 6 below. Of the 12,146 alive patients, based on the estimated mortality rate, 2,662 (21.9%) patients were predicted to die within 1 year. The drop in the testing set in 2018 is due to insufficient follow-up duration (<1 year) for alive patients as of the data collection date (Feb. 9, 2019).

TABLE 6

| | Training | | | Testing | | |
|---|---|---|---|---|---|---|
| Year | All | Dead | Alive | All | Dead | Alive |
| 2010 | 109,711 | 28,005 | 81,706 | 3,841 | 685 | 3,156 |
| 2011 | 143,659 | 35,552 | 108,107 | 4,441 | 903 | 3,538 |
| 2012 | 189,711 | 46,572 | 143,139 | 5,382 | 1,053 | 4,329 |
| 2013 | 240,825 | 58,765 | 182,060 | 6,632 | 1,248 | 5,384 |
| 2014 | 301,471 | 72,965 | 228,506 | 7,670 | 1,480 | 6,190 |

TABLE 6-continued

| | Training | | | Testing | | |
|---|---|---|---|---|---|---|
| Year | All | Dead | Alive | All | Dead | Alive |
| 2015 | 375,567 | 90,717 | 284,850 | 8,378 | 1,481 | 6,897 |
| 2016 | 459,659 | 109,493 | 350,166 | 8,986 | 1,371 | 7,615 |
| 2017 | 553,164 | 128,405 | 424,759 | 10,243 | 1,542 | 8,701 |
| 2018 | 657,322 | 150,800 | 506,522 | 4,653 | 1,351 | 3,302 |

Artificially closing the 5 care gaps that positively associated with mortality resulted in 2,495 (20.5%) patients being predicted to die within 1 year. This resulted in a predicted absolute risk reduction of 1.4% (range: 0-31%, absolute) in mortality rate, and 167 (6.3% of 2,662) additional patients would be expected to survive beyond 1 year assuming all 5 care gaps could be closed.

The relationship between risk and benefit (risk reduction) was further investigated by comparing the predicted benefits among several subgroups. FIG. 6A is a scatter plot of risk score and corresponding benefit for individual patients in the prediction set (N=12,146). Negative reductions in mortality rate reflect a detrimental effect of closing care gaps on mortality risk as predicted by the non-linear XGBoost model in a small proportion of patients. FIG. 6B is a graph of average mortality rate before and after care gap closure simulation in selected groups. Note that risk is not equivalent to benefit since patients at similarly high mortality risk levels do not have the same predicted benefit of closing care gaps.

FIG. 6B shows that the overall average benefit ("Overall Average") was predicted to be relatively small and was primarily driven by the large group of patients with low mortality risk at baseline (risk score <0.2) as well as low benefit after closing the care gaps (<5% reduction in mortality rate) ("Low Risk, Low Benefit"). There was, however, a subgroup of patients predicted to be high risk for mortality (risk score >0.5) who were also predicted to have high benefit after closing gaps (>10% reduction in mortality rate, "High Risk, High Benefit"). Yet, not all high-risk patients were predicted to have high benefit, as evidenced by another subgroup of patients who had similarly high risk at baseline but minimal risk reduction after closing the care gaps ("High Risk, Low Benefit").

Patient Prioritization to Efficiently Close Care Gaps Through Population Health Management Assuming that a population health management team could be assembled and deployed to close care gaps, the efficiency of its efforts would depend on effective guidance as to which patients to target first in a rank ordered fashion. To demonstrate the potential value of machine learning to optimize care team resource deployment in this setting, the number of lives predicted to be saved versus the number of patients receiving an intervention (in which all eligible gaps were subsequently assumed closed) was plotted for several different prioritization strategies:

Strategy 1: Random prioritization

Strategy 2: Randomly prioritizing any patient with at least one open care gap

Strategy 3: Rank ordering patients by the number of open care gaps

Strategy 4: Stratifying patients using the Seattle Heart Failure risk score

Strategy 5: Stratifying patients according to the XGBoost model's predicted "benefit" (i.e. mortality risk reduction)

Figure 7:
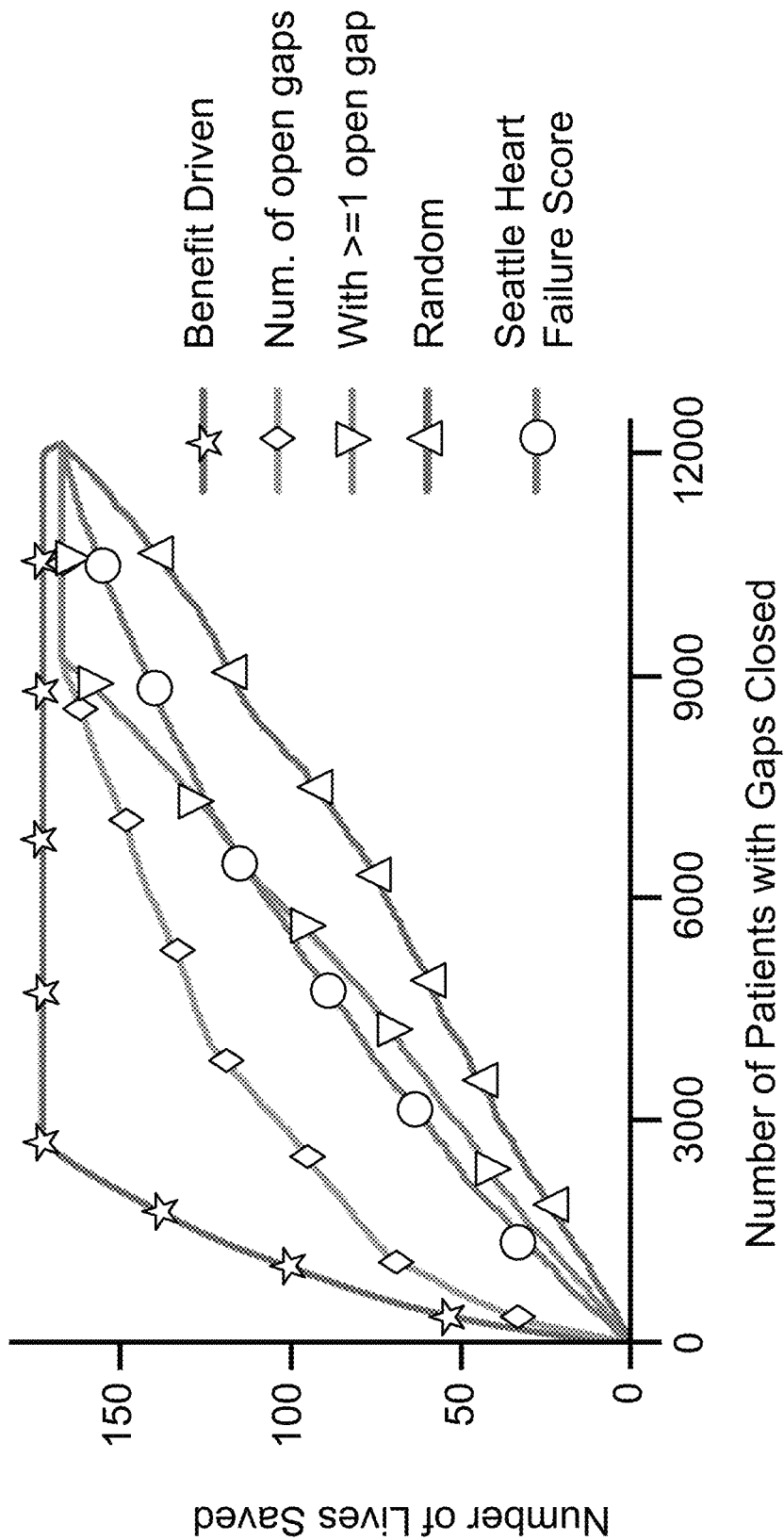
FIG. 7 is a graph of estimated lives saved by various stratification techniques during simulation of care gap closure using XGBoost.

FIG. 7 is a graph of estimated lives saved by various stratification techniques during simulation of care gap closure using XGBoost. Prioritization of patients according to predicted benefit is the most efficient resource allocation method based on having the highest predicted patient survival (y-axis) relative to the number of patients needed to treat (x-axis). Note that the slopes of the plotted lines are inversely proportional to the number needed to treat and thus steeper lines represent more efficient patient prioritization. The small drop in lives saved at the far right-hand side of the line corresponding to the "Benefit Driven" model reflects the patients in which closing the care gaps had a predicted negative impact on mortality risk, as shown in FIG. 6A.

FIG. 7 demonstrates that the proposed machine learning benefit stratification model (strategy 5) was the most efficient. That is, benefit stratification had the steepest slope of any prioritization strategy and thus, in a resource constrained environment, maximized the predicted total number of lives saved for a given number of patient interventions.

Discussion

Optimized population health management demands novel, data-driven approaches for allocating healthcare resources, particularly within new value-based care models. This study has made considerable advances toward the development of such an approach for heart failure that combines extensively and carefully curated clinical data and machine learning. The model incorporates important clinical variables, quantitative measures from common diagnostic studies such as echocardiography and electrocardiograms, as well as evidence-based interventions in the form of "care gaps". The results show that a machine learning model with these inputs can achieve good accuracy to predict 1-year all-cause mortality in patients with heart failure. Furthermore, the explicit representation of clinical care gaps in the model represents a new paradigm for guiding clinical action with machine learning. Specifically, the present disclosure shows how these care gap inputs can be used to predict risk reduction associated with specific interventions on an individual patient level.

These model predictions can provide guidance to integrated health systems working to efficiently distribute scarce clinical resources (e.g., care teams) to patients who need them the most. Importantly, most published models and clinical scoring systems rely heavily on risk prediction, which could be used to prioritize distribution of healthcare resources. However, risk is not equivalent to benefit and thus patients with identical risk of 1-year mortality can have very different predicted benefit from interventions. Thus, deployment of resources based simply on risk is unlikely to be efficient, as demonstrated by the superiority of the predictive model's predicted performance over the Seattle Heart Failure score for prioritizing patient interventions.

Comparison to Other Predictive Machine Learning Models in Heart Failure

Several studies have been published in recent years using machine learning to predict outcomes (mostly survival) in patients with heart failure. These studies used various methods, from traditional classification (e.g. logistic regression, random forest) to custom developed algorithms (Contrast pattern aided logistic regression with probabilistic loss function) to predict mortality in heart failure. The reported accuracies (AUC) vary from 0.61-0.94, while mostly centered around 0.75-0.8.

On the surface, the model performance is comparable with these prior studies. However, several critical differences should be noted, as they reflect the more challenging prediction task accomplished by the predictive model presented by this disclosure. First, the model was designed for prospective implementation in a "real world" clinical setting, as reflected in both the training/testing scheme and the prospective randomized clinical trial initiated using this model. Hence, the approach relied on clinical EHR data (as opposed to data collected during a controlled clinical trial) and allowed for its associated challenges (e.g., incomplete and/or erroneous data). Second, most previous studies have focused on specific subgroups of heart failure, such as stratifications by preserved) or reduced ejection fraction or patients with acute decompensation; or focused on prediction in specific settings, such as in-hospital mortality or mortality following admission. Tur analysis focused broadly on all patients with heart failure and considered both in-patient and out-patient encounters, again reflecting the needs of a continuously updating population health management approach.

Given this more challenging prediction task, it is noteworthy that the model performance was in line with previous studies. This achievement was driven primarily by two attributes of the dataset. Foremost, the sample size of the study is more than an order of magnitude larger (close to 1 million encounters from 24 thousand patients) compared to previous studies (mostly a few hundreds to thousands), which allows for more generalizable models with reduced chance of overfitting. Additionally, the model included a comprehensive set of patient features (input variables), including data from diagnostic studies such as echocardiograms, which are highly important for predicting all-cause mortality in the setting of heart failure (FIG. 4) and a more general cardiology population (note that the current study contains some patients from a previous study on 171,510 patients). In contrast, most previous studies were limited to basic clinical information (demographics, vital signs), results from lab tests, and co-morbidities. Only one study included additional diagnostic measures from echocardiography and electrocardiograms and reported an AUC of 0.72 for all-cause mortality despite a small patient sample (n=397), further supporting the importance of these quantitative diagnostic data.

Another major drawback of most prior studies is the lack of actionable model results which can be used clinically. Therefore, although a large number of accurate models have been developed over the last decade to predict outcomes in patients with heart failure, few have truly impacted clinical practice. A recent study attempted to address this issue by evaluating associations between treatments (various medications) and outcomes among 4 subgroups of heart failure identified using unsupervised clustering in a retrospective dataset. The authors of the study showed marked differences in outcomes and different responses to medications among the 4 subgroups, which could help to define effective treatment strategies specific to each subgroup. In line with that study, this concept was taken one step further and 6 evidence-based interventions (care gaps) were introduced into the machine learning model and used these variables as actionable "levers" in the model to predict individual patient outcomes after a clinical action. By artificially closing these care gaps, it is predicted that an additional 167 patients could survive longer than 1 year.

Despite the fact that these interventions (care gaps) are recommended in national guidelines based on demonstrated benefit (e.g. even flu vaccination has been associated with decreased all-cause mortality in heart failure), the prevalence of open care gaps remains a significant problem in medicine. For example, in patients with heart failure, therapies proven to prolong life are used at staggeringly low rates: only 57% are receiving ACE inhibitors, 34% are receiving evidence-based beta blockers, and 32% are receiving mineralocorticoid antagonists. This problem is highly complex and unlikely to be solved by relying on individual providers to change practice. However, new value-based care models can likely address this problem more effectively by creating organized care teams. These teams will require accurate, reliable data science, such as that presented in this disclosure, in order to successfully allocate resources.

Surprisingly, the "BP in goal" care gap had a negative relationship with outcome, in contradiction to the evidence-based guidelines based on observational studies which have shown that lower blood pressures associated with reduced risk of adverse events in heart failure. However, the "blood pressure paradox" has also been noted in multiple studies where lower blood pressure or pronounced changes in blood pressure (increases or decreases) was associated with poor outcomes. In the current study, the linear logistic regression model demonstrated an inconsistent relationship between blood pressure and survival, i.e. negative association in some training years and positive association in others, with a small, negative relationship on average (data not shown). In the present disclosure, a machine learning model configured to predict 1-year all-cause mortality with good accuracy in a large cohort of patients with heart failure is presented. The results leveraging nearly 1 million encounters from over 24,000 patients show that these models can be used to not only risk stratify patients, but to also efficiently prioritize patients based on predicted benefits of clinically relevant evidence-based interventions. This approach will likely prove useful for assisting heart failure population health management teams within new value-based payment models. It is also contemplated that a model configured to predict all-cause mortality for time periods other than one year, including six months, two years, three years, four years, five year, or other appropriate time periods could also be generated. Additionally, as described above, additional clinically relevant endpoints can be used to train the predictive machine learning model.

Figure 8:
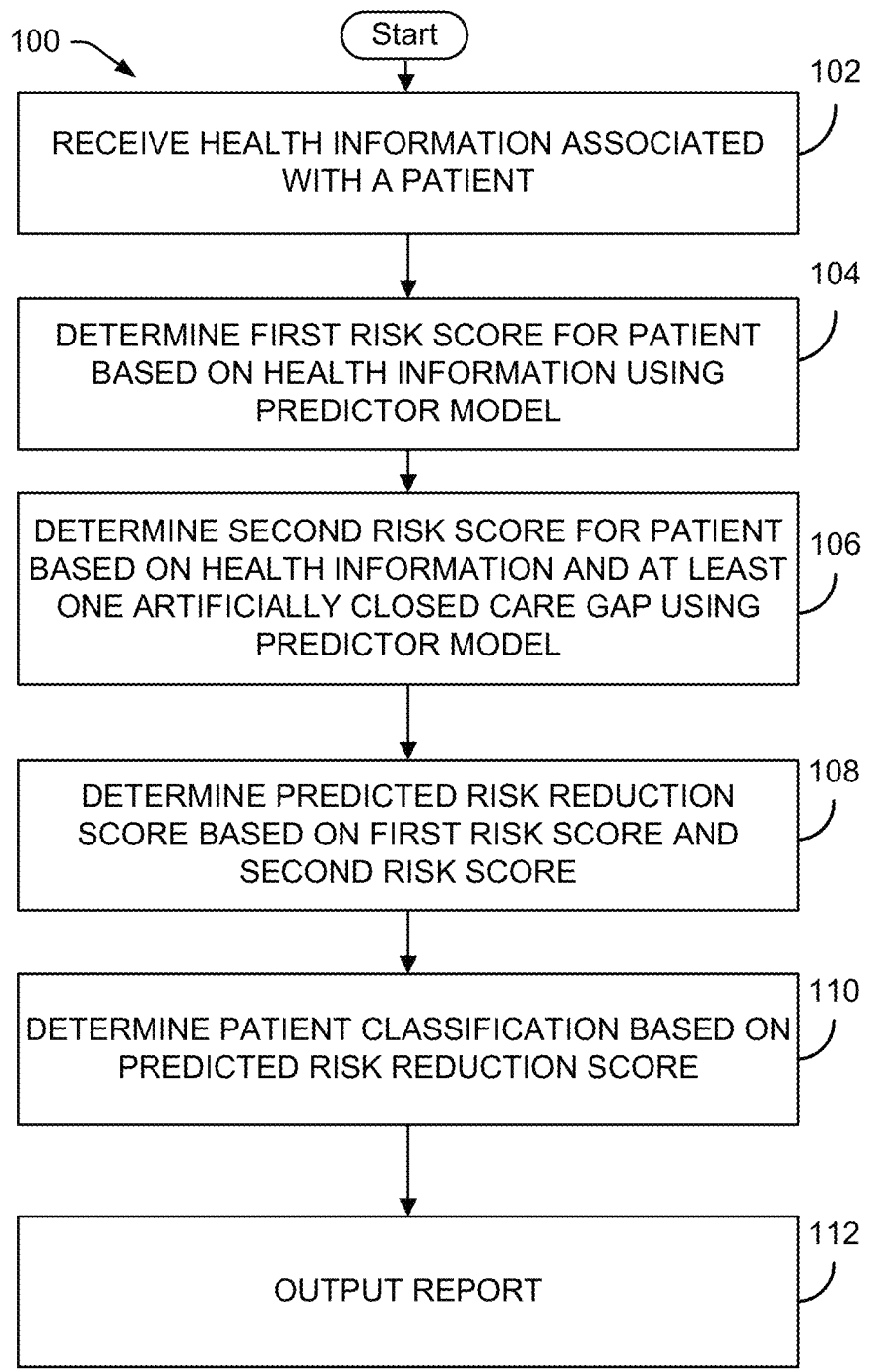
FIG. 8 is an exemplary process for predicting all-cause mortality in patients with heart failure for a predetermined time period (i.e., one year), as well as providing treatment recommendations for a patient to a physician.

Turning now to FIG. 8, an exemplary process 100 for predicting all-cause mortality in patients with heart failure for a predetermined time period (i.e., one year), as well as providing treatment recommendations for a patient to a physician is shown. The process 100 predicts risk scores for the patient based on a machine learning model trained on clinical variables (e.g. demographics and labs), electrocardiogram measurements, electrocardiograph measurements, and evidence-based care gap variables as described above. The process 100 can be employed in a population health analytics module that is relied on by a care team including the physician to prioritize patients who should be but are not receiving evidence-based care.

At 102, the process 100 can receive health information associated with the patient. The health information can include at least a portion of an EHR associated with the patient. The EHR can be stored in a database of a provider. In some embodiments, the health information can include the eighty variables including eight clinical variables (age, sex, height, weight, smoking status, heart rate, systolic and diastolic blood pressures), use of loop diuretics, twelve biomarkers (hemoglobin, eGFR, CKMB, lymphocytes, HDL, LDL, uric acid, sodium, potassium, NT-proBNP, troponin T, A1c), forty-four non-redundant echocardiographic variables, nine ECG measurements (such as QRS duration) and the six care gap variables described above. In some embodiments, the health information may not include BP in goal. The process 100 can then proceed to 104.

At 104, the process 100 can determine a first risk score for the patient based on the health information using a trained predictor model. The trained predictor model can be a linear model such as linear logistic regression or a non-linear model such as random forest or XGBoost as described above. The predictor model can be trained to predict risk scores of all-cause mortality for a predetermined time period, such as one year, although it is appreciated that the model could be trained to predict all-cause mortality for other time periods six months, two years, three years, four years, five year, or other appropriate time periods or other appropriate clinical endpoints. The process 100 can provide at least a portion of the health information to the model and receive the first risk score from the model. The first risk score can represent a baseline score corresponding to an actual predicted mortality risk of the patient. The process 100 can then proceed to 106.

At 106, the process 100 can determine a second risk score for the patient based on the health information and at least one artificially closed care gap included in the health information using the predictor model. The process 100 can artificially close appropriate care gaps by changing the value of each open care gap from 1=open/untreated to 0=closed/treated while keeping all other variables included in the health information unchanged. The process 100 may not close certain care gaps in patients who meet the exclusion criteria for that care gap. For example, a patient with bradycardia who could not be treated with EBBB would not have the EBBB care gap closed. The process 100 can then provide the health information, which has been modified to close any appropriate care gaps, to the model and receive the second risk score from the model. The second risk score can represent a simulated score corresponding to what the predicted mortality risk of the patient would be if all appropriate open care gaps are closed. For some patients, at 106, the process may not be able to close any care gaps, either because the care gaps are already closed or cannot be closed for patient who meet the exclusion criteria for certain care gaps as described above, in which case the second risk score will be the same as the first risk score. The process 100 can then proceed to 108.

At 108, the process 100 can determine a predicted risk reduction score based on the first risk score and the second risk score. The process 100 can calculate the predicted risk reduction score by determining the difference between the first risk score and the second risk score. The process 100 can then proceed to 110.

At 110, the process 100 can determine a patient classification based on the predicted risk reduction score. The process 100 can determine the patient classification by comparing the predicted risk reduction score of the patient against predicted risk reduction scores of a group of other patients. The group of other patients can include other patients treated by the provider. The process 100 can determine a rank of the patient predicted risk reduction score of the patient compared to the group of patients (i.e., using strategy 5 described above). For example, the process 100 can determine that the predicted risk reduction score of 0.3 is the five hundredth highest predicted risk reduction score out of ten thousand patients. The process 100 can then proceed to 112.

At 112, the process 100 can generate and output a report based on at least one of the first risk score, the second risk score, or the predicted risk reduction score. For example, the report can include the raw first risk score, the raw second risk score, and the raw predicted risk reduction score. The report can include the raw rank of the predicted risk reduction score of the patient compared to the group of patients (e.g., that the predicted risk reduction score is the five hundredth highest predicted risk reduction score out of ten thousand patients) or a percentile rank of the predicted risk reduction score (e.g., that the predicted risk reduction score is in the ninety-fifth percentile of all patients of the provider). The report can include any appropriate graphs and/or charts generated based on the first risk score, the second risk score, and/or the predicted risk reduction score. The report can be displayed to a physician using a display such as a computer monitor or a screen integral to a tablet computer, smartphone, laptop computer, etc. In some embodiments, the report can be output to a storage device including a memory. In some embodiments, the report can include the raw first risk score and the second raw risk score. The first risk score and the second risk score can be used by a physician and/or a provider to estimate the risk of death of the patient. In this way, the physician and/or provider can estimate if the patient has a high likelihood of dying within the year (or other time period) so that appropriate resources such as palliative care physicians can be provided to the patient at an appropriate time.

Turning now to FIG. 9, an exemplary system 210 for implementing the aforementioned disclosure is shown. The system 210 may include one or more computing devices 212a, 212b in communication with one another, as well as with a server 214 and one or more databases or other data repositories 216, e.g., via Internet, intranet, ethernet, LAN, WAN, etc. The computing devices also may be in communication with additional computing devices 212c, 212d through a separate network 218. Although specific attention is paid to computing device 212a, each computing device may include a processor 220, one or more computer readable medium drive 222, a network interface 224, and one or more I/O interfaces 226. The device 212a also may include memory 228 including instructions configured to cause the processor to execute an operating system 230 as well as a population health analytics module 232 for predicting 1-year all-cause mortality in patients with heart failure as well as providing treatment recommendations for a patient to a physician as described herein. The population health analytics module 232 can be used to execute at least a portion of the process 100 described above in conjunction with FIG. 8.

The methodology described above for driving clinical action based on predicted reduction in risk (i.e., benefit) can be applied to the management of any particular population (other than a heart failure population) in healthcare including but not limited to diabetes, pulmonary disease, renal disease, rheumatologic disorders, musculoskeletal conditions, endocrinopathies, etc. Furthermore, the methodology can be extended to predict risk reduction for any particular clinical outcome of interest, including but not limited to outcomes such as mortality, additional adverse clinical events such as stroke or heart attack, hospitalization, total cost of care or other healthcare utilization metrics, etc.

Thus, as described herein, the present disclosure provides systems and methods for providing clinically-relevant, actionable treatment recommendations for patients who should be but are not receiving evidence-based care generalizable to a broad and heterogeneous heart failure population.

While the present disclosure may be susceptible to various modifications and alternative forms, specific embodiments have been shown by way of example in the drawings and have been described in detail herein. However, it should be understood that the present disclosure is not intended to be limited to the particular forms disclosed. Rather, the present disclosure is to cover all modifications, equivalents, and alternatives falling within the spirit and scope of the present disclosure as defined by the following appended claims.

This written description uses examples to disclose the present disclosure, including the best mode, and also to enable any person skilled in the art to practice the present disclosure, including making and using any devices or systems and performing any incorporated methods. The patentable scope of the present disclosure is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this present disclosure.

What is claimed is:

1. A method for providing treatment recommendations for a patient to a physician, the method comprising:
   receiving health information associated with the patient, the health information comprising a plurality of input variables for a trained predictive machine learning model, wherein the trained predictive machine learning model incorporates clinical variables and care gap variables, at least some of the plurality of input variables associated with a respective first value reflecting a state thereof;
   identifying a plurality of open care gaps within the health information, each open care gap comprising an input variable of the plurality of input variables for which the respective first value corresponds to an open state;
   determining, using the trained predictive machine learning model, a first risk score relating to a clinical endpoint of the patient, based on the health information including one or more of the plurality of open care gaps in the open state;
   modifying, for at least one of the open care gaps, the first value to be a second value reflecting an artificially closed status of the care gap in the health information;
   determining, using the trained predictive machine learning model with the second value as one of the input variables instead of the first value, a second risk score for the patient;
   determining a predicted risk reduction score based on the first risk score and the second risk score;

determining a patient classification based on the predicted risk reduction score, the patient classification comprising both a risk component related to the first risk score and a benefit component related to the second risk score; and outputting a report based on at least one of the first risk score, the second risk score, or the predicted risk reduction score.

2. The method of claim 1, wherein the health information includes diagnostic studies.

3. The method of claim 1, further comprising:
prior to determining the first risk score, removing redundant health information and removing physiologically impossible health information.

4. The method of claim 1, further comprising:
prior to determining the first risk score, imputing missing health information using one or more of linear interpolation from related health information or robust multivariate imputation by chained equations.

5. The method of claim 1, further comprising:
prior to determining the first risk score, discarding health information for which at least a threshold number of samples is missing.

6. The method of claim 1, wherein the predictive machine learning model is a linear model.

7. The method of claim 6, wherein the linear model is a linear logistic regression model.

8. The method of claim 1, wherein the predictive machine learning model is a non-linear model.

9. The method of claim 8, wherein the non-linear model is one of random forest or XGBoost.

10. The method of claim 1, wherein the at least one of the open care gaps comprises a plurality of care gaps.

11. The method of claim 1, wherein the trained predictive machine learning model is selected from among a plurality of trained predictive machine learning models.

12. The method of claim 11, wherein a split-by-year procedure applied to each trained predictive machine learning model of the plurality of trained predictive machine learning models is used to determine which model is a best model.

13. The method of claim 12, wherein the best model is retrained using an optimal set of hyper-parameters.

14. The method of claim 1, wherein the step of determining a patient classification comprises comparing the predicted risk reduction score against predicted risk reduction scores of a plurality of other patients.

15. The method of claim 14, wherein the step of determining a patient classification further comprises ranking the patient relative to the plurality of other patients.

16. The method of claim 1, wherein the patient is part of a heart failure population of patients.

17. The method of claim 1, wherein the patient is part of a population of at least one of diabetes, pulmonary disease, renal disease, rheumatologic disorders, musculoskeletal conditions, or endocrinopathies patients.

18. The method of claim 1, wherein the first risk score, the second risk score, and the predicted risk reduction score relate to the clinical endpoint occurring within a predetermined period of time.

19. The method of claim 18, wherein the clinical endpoint is mortality of the patient.

20. The method of claim 18, wherein the predetermined period of time is 1 year.

21. The method of claim 18, wherein the second value has a positive relationship with respect to the clinical endpoint.

22. The method of claim 1, wherein the patient classification includes evaluating the predicted risk reduction score relative to a number of patients needed to treat.

23. The method of claim 1, wherein the report includes treatment recommendations for the patient.

24. The method of claim 23, wherein the treatment recommendations include palliative care.

25. The method of claim 1, further comprising:
allocating resources to the patient based on the patient classification.

26. The method of claim 1, wherein the trained predictive machine learning model is used in the step of determining a patient classification based on the predicted risk reduction score.

27. A method for providing treatment recommendations for a patient to a physician, the method comprising:
receiving health information associated with the patient, the health information comprising a plurality of input variables for a trained predictive machine learning model, at least some of the plurality of input variables associated with a respective first value reflecting a state thereof, wherein the trained predictive machine learning model is trained on a dataset derived from EHR records of a patient training dataset and incorporates clinical variables and care gap variables;

identifying a plurality of open care gaps within the health information, each open care gap comprising an input variable of the plurality of input variables for which the respective first value corresponds to an open state;

determining, using the trained predictive machine learning model, a first risk score for the patient relating to a clinical endpoint of the patient, based on the health information including one or more of the plurality of open care gaps in the open state using the trained predictive machine learning model trained on a dataset derived from EHR records of a patient training dataset, wherein the trained predictive machine learning model is a best model selected from among a plurality of trained predictive machine learning models;

modifying, for at least one of the open care gaps, the first value to be a second value reflecting an artificially closed status of the care gap in the health information;

determining, using the trained predictive machine learning model with the second value as one of the input variables instead of the first value, determining a second risk score for the patient based on the health information and at least one artificially closed care gap included in the health information using the predictive machine learning model;

determining a predicted risk reduction score based on the first risk score and the second risk score;

determining a patient classification based on the predicted risk reduction score, the patient classification comprising both a risk component related to the first risk score and a benefit component related to the second risk score; and outputting a report based on at least one of the first risk score, the second risk score, or the predicted risk reduction score.

28. A method for providing treatment recommendations for a patient to a physician, the method comprising:
receiving health information associated with the patient, the health information comprising a plurality of input variables for a trained predictive machine learning model, at least one of the plurality of input variables associated with a respective first value reflecting a state thereof;

identifying a plurality of open care gaps within the health information, each open care gap comprising an input variable of the plurality of input variables for which the respective first value corresponds to an open state;

determining, using the trained predictive machine learning model that incorporates clinical variables and care gap variables, a first risk score for the patient relating to a clinical endpoint of the patient based on the health information including one or more of the plurality of open care gaps in the open state using the trained predictive machine learning model, wherein the trained predictive machine learning model is a best model selected from among a plurality of trained predictive machine learning models;

supplementing, by the trained predictive machine learning model, the health information to artificially close at least one care gap included in the health information artificially change the first value to be a second value reflecting an artificially closed status of the care gap in the health information;

determining, using the trained predictive machine learning model with the second value as one of the input variables instead of the first value, determining a second risk score for the patient based on the supplemented health information using the predictive machine learning model;

determining a predicted risk reduction score based on the first risk score and the second risk score;

determining a patient classification based on the predicted risk reduction score, the patient classification comprising both a risk component related to the first risk score and a benefit component related to the second risk score; and outputting a report based on at least one of the first risk score, the second risk score, or the predicted risk reduction score.

* * * * *